(12) United States Patent
Kamatani et al.

(10) Patent No.: US 9,019,328 B2
(45) Date of Patent: Apr. 28, 2015

(54) ORGANIC COMPOUND, ORGANIC LIGHT-EMITTING DEVICE, AND DISPLAY APPARATUS

(75) Inventors: Jun Kamatani, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/346,291

(22) PCT Filed: Sep. 5, 2012

(86) PCT No.: PCT/JP2012/073244
§ 371 (c)(1),
(2), (4) Date: Mar. 20, 2014

(87) PCT Pub. No.: WO2013/042584
PCT Pub. Date: Mar. 28, 2013

(65) Prior Publication Data
US 2014/0225968 A1   Aug. 14, 2014

(30) Foreign Application Priority Data
Sep. 22, 2011  (JP) .................................. 2011-207325

(51) Int. Cl.
*B41J 2/39* (2006.01)
*B41J 2/45* (2006.01)
(Continued)

(52) U.S. Cl.
CPC ................ *B41J 2/45* (2013.01); *C07C 211/61* (2013.01); *C07C 13/62* (2013.01); *C07C 17/263* (2013.01); *C07C 25/22* (2013.01); *C09K 11/06* (2013.01); *C07D 209/86* (2013.01); *C07D 213/24* (2013.01); *H01L 51/0056* (2013.01); *H01L 51/0058* (2013.01); *H01L 51/006* (2013.01); *H01L 51/0072* (2013.01); *C07C 255/50* (2013.01); *C07C 321/30* (2013.01); *C07F 7/0809* (2013.01); *H01L 51/0067* (2013.01); *H01L 51/0068* (2013.01); *H01L 51/0094* (2013.01); *H01L 51/5004* (2013.01); *H01L 51/5024* (2013.01); *H01L 51/504* (2013.01); *C09B 57/00* (2013.01); *C07C 43/205* (2013.01); *C07C 2103/54* (2013.01);
(Continued)

(58) Field of Classification Search
USPC ...................... 347/112, 130, 129, 238; 357/40
See application file for complete search history.

(56) References Cited

U.S. PATENT DOCUMENTS

2013/0048966 A1* 2/2013 Horiuchi et al. ................. 257/40
2014/0291660 A1* 10/2014 Takaku et al. ................... 257/40

FOREIGN PATENT DOCUMENTS

CN          101541714 A    9/2009
JP          2002-110354 A  4/2002
(Continued)

*Primary Examiner* — Kristal Feggins
(74) *Attorney, Agent, or Firm* — Canon U.S.A. Inc., IP Division

(57) ABSTRACT

The present invention provides a novel organic compound having a high quantum yield and a high color purity. Provided is an organic compound represented by Formula (1) described in Claim 1. In Formula (1), $R_1$ to $R_{20}$ are each independently selected from hydrogen atoms, halogen atoms, substituted or unsubstituted alkyl groups, substituted or unsubstituted alkoxy groups, substituted or unsubstituted amino groups, substituted or unsubstituted aryl groups, substituted or unsubstituted heterocyclic groups, substituted or unsubstituted aryloxy groups, substituted or unsubstituted thiol groups, silyl groups, and cyano groups.

16 Claims, 3 Drawing Sheets

(51) Int. Cl.
*C07C 211/61* (2006.01)
*C07C 13/62* (2006.01)
*C07C 17/263* (2006.01)
*C07C 25/22* (2006.01)
*C09K 11/06* (2006.01)
*C07D 209/86* (2006.01)
*C07D 213/24* (2006.01)
*H01L 51/00* (2006.01)
*C07C 255/50* (2006.01)
*C07C 321/30* (2006.01)
*C07F 7/08* (2006.01)
*H01L 51/50* (2006.01)
*C09B 57/00* (2006.01)
*C07C 43/205* (2006.01)

(52) U.S. Cl.
CPC ............... *C09K 2211/1011* (2013.01); *C09K 2211/1029* (2013.01); *C07C 2102/42* (2013.01); *C07C 2103/26* (2013.01); *H01L 51/0061* (2013.01); *C07C 2101/14* (2013.01)

(56) References Cited

FOREIGN PATENT DOCUMENTS

| | | |
|---|---|---|
| JP | 2008-255095 A | 10/2008 |
| JP | 2009-149612 A | 7/2009 |
| JP | 2009-182039 A | 8/2009 |
| JP | 2012149012 * | 8/2012 ............. C07C 13/62 |

* cited by examiner

ORGANIC COMPOUND, ORGANIC LIGHT-EMITTING DEVICE, AND DISPLAY APPARATUS

TECHNICAL FIELD

The present invention relates to a novel organic compound and an organic light-emitting device and a display apparatus having the compound.

BACKGROUND ART

An organic light-emitting device (also referred to as organic electroluminescent device or organic EL device) is an element including a pair of electrodes and an organic compound layer disposed between these electrodes.

Electrons and holes are injected from the pair of electrodes into the organic compound layer to generate excitons of the light-emitting organic compound in the organic compound layer, and the organic light-emitting device emits light when the excitons return to the ground state.

The organic light-emitting devices have remarkably progressed recently, and low driving voltages, various emission wavelengths, rapid response, and reductions in size and weight of light-emitting devices are possible.

In order to provide high-performance organic light-emitting devices, creation of compounds having excellent light-emitting characteristics and carrier-transporting properties is important. Accordingly, organic compounds for organic light-emitting devices have been actively being created.

As compounds that have been created until now, for example, Compound 1-A disclosed in PTL 1 as a synthetic intermediate and in PTL 2 as an organic transistor material is known.

[Chem. 1]

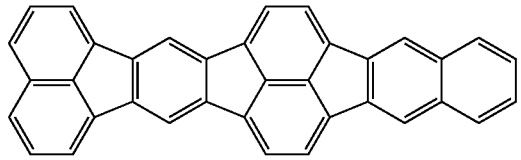

1-A

Data of light-emitting characteristics of Compound 1-A is not described, but the luminescent color is yellow, and the emission intensity is too low to hardly emit light.

The basic skeleton of the compound described in PTL 1 emits yellow light as described above. In addition, light emission with a high quantum yield is not obtained.

CITATION LIST

Patent Literature

PTL 1 Japanese Patent Laid-Open No. 2002-110354 (no corresponding foreign application)
PTL 2 Japanese Patent Laid-Open No. 2009-182039 (no corresponding foreign application)

SUMMARY OF INVENTION

The present invention provides an organic compound that has a high quantum yield and emits light in a green region by its basic skeleton only.

Accordingly, the present invention provides an organic compound represented by the following Formula (1).

[Chem. 2]

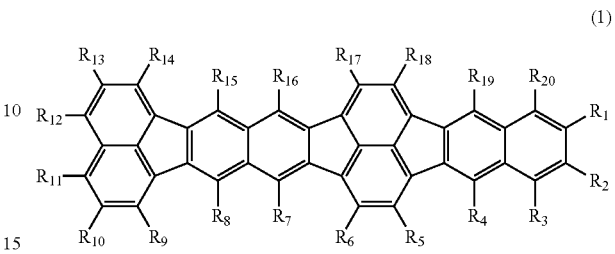

(1)

In Formula (1), $R_1$ to $R_{20}$ are each independently selected from hydrogen atoms, halogen atoms, substituted or unsubstituted alkyl groups, substituted or unsubstituted alkoxy groups, substituted or unsubstituted amino groups, substituted or unsubstituted aryl groups, substituted or unsubstituted heterocyclic groups, substituted or unsubstituted aryloxy groups, substituted or unsubstituted thiol groups, silyl groups, and cyano groups.

The present invention can provide an organic compound capable of emitting light in a green region by the basic skeleton itself and capable of having a high quantum yield. The present invention also can provide an organic light-emitting device including the compound and thereby having a high luminous efficiency.

DESCRIPTION OF EMBODIMENT

Figure 1:
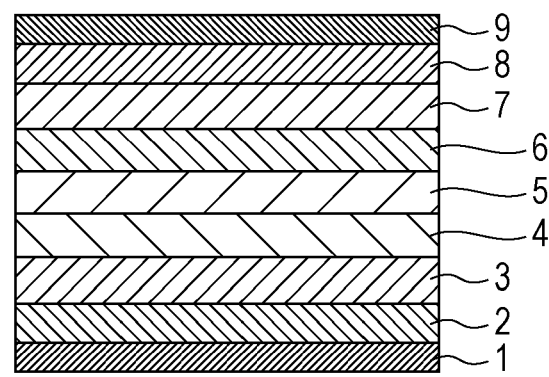
FIG. 1 is a schematic diagram illustrating an example of a light-emitting layer lamination type organic light-emitting device according to an embodiment.

The present invention relates to the organic compound represented by the following Formula (1).

[Chem. 3]

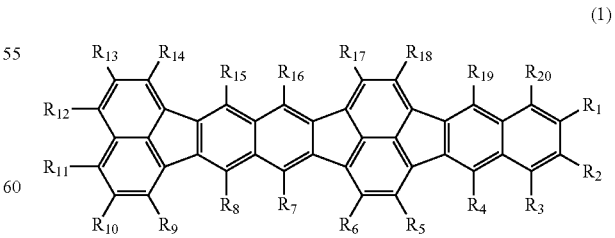

(1)

In Formula (1), $R_1$ to $R_{20}$ are each independently selected from hydrogen atoms, halogen atoms, substituted or unsubstituted alkyl groups, substituted or unsubstituted alkoxy groups, substituted or unsubstituted amino groups, substituted or unsubstituted aryl groups, substituted or unsubstituted heterocyclic groups, substituted or unsubstituted aryloxy groups, substituted or unsubstituted thiol groups, silyl groups, and cyano groups.

In one aspect, $R_1$ to $R_{20}$ in Formula (1) are each independently selected from hydrogen atoms, substituted or unsubstituted alkyl groups, and substituted or unsubstituted aryl groups.

Examples of the halogen atoms represented by $R_1$ to $R_{20}$ include, but not limited to, fluorine, chlorine, bromine, and iodine.

Examples of the alkyl groups represented by $R_1$ to $R_{20}$ include, but not limited to, methyl, ethyl, n-propyl, iso-propyl, n-butyl, sec-butyl, tert-butyl, octyl, cyclohexyl, 1-adamantyl, and 2-adamantyl groups.

Examples of the alkoxy groups represented by $R_1$ to $R_{20}$ include, but not limited to, methoxy, ethoxy, propoxy, 2-ethyl-octyloxy, and benzyloxy groups.

Examples of the amino groups represented by $R_1$ to $R_{20}$ include, but not limited to, N-methylamino, N-ethylamino, N,N-dimethylamino, N,N-diethylamino, N-methyl-N-ethylamino, N-benzylamino, N-methyl-N-benzylamino, N,N-dibenzylamino, anilino, N,N-diphenylamino, N,N-dinaphthylamino, N,N-difluorenylamino, N-phenyl-N-tolylamino, N,N-ditolylamino, N-methyl-N-phenylamino, N,N-dianisolylamino, N-mesityl-N-phenylamino, N,N-dimesitylamino, N-phenyl-N-(4-tert-butylphenyl)amino, N-phenyl-N-(4-trifluoromethylphenyl)amino, and N-piperidyl groups.

Examples of the aryl groups represented by $R_1$ to $R_{20}$ include, but not limited to, phenyl, naphthyl, indenyl, biphenyl, terphenyl, and fluorenyl groups.

Examples of the heterocyclic groups represented by $R_1$ to $R_{20}$ include, but not limited to, pyridyl, oxazolyl, oxadiazolyl, thiazolyl, thiadiazolyl, carbazolyl, acridinyl, and phenanthrolyl groups.

Examples of the aryloxy groups represented by $R_1$ to $R_{20}$ include, but not limited to, phenoxy and thienyloxy groups.

Examples of the silyl groups represented by $R_1$ to $R_{20}$ include, but not limited to, a triphenylsilyl group.

Examples of the substituents which may be possessed by the alkyl groups, alkoxy groups, amino groups, aryl groups, heterocyclic groups, and aryloxy groups include, but not limited to, alkyl groups such as methyl, ethyl, n-propyl, iso-propyl, n-butyl, and tert-butyl groups; aralkyl groups such as a benzyl group; aryl groups such as phenyl and biphenyl groups; heterocyclic groups such as pyridyl and pyrrolyl groups; amino groups such as dimethylamino, diethylamino, dibenzylamino, diphenylamino, and ditolylamino groups; alkoxy groups such as methoxy, ethoxy, and propoxy groups; aryloxy groups such as a phenoxy group; halogen atoms such as fluorine, chlorine, bromine, and iodine; and a cyano group.

In this embodiment, $R_1$ to $R_{20}$ in Formula (1) can be each independently selected from hydrogen atoms, substituted or unsubstituted alkyl groups, and substituted or unsubstituted aryl groups.

The organic compound according to the embodiment can inhibit concentration quenching by introducing a substituent to the basic skeleton. Such a compound shows high sublimability in sublimation and high solubility in a solvent for coating.

From the viewpoint of inhibiting the concentration quenching, at least one of $R_1$ to $R_{20}$ in Formula (1) may be substituted with an alkyl group.

The basic skeleton in the embodiment is a fused-ring structure having a conjugated structure. That is, the basic skeleton of the organic compound according to the embodiment has a structure represented by the compound where $R_1$ to $R_{20}$ in Formula (1) are all hydrogen atoms.

Properties of the basic skeleton of the organic compound according to the embodiment will now be described.

The present inventors have focused on the basic skeleton itself in designing the organic compound represented by Formula (1). Specifically, the inventors have tried to provide a compound where the molecule of the basic skeleton only has an emission wavelength within a desired emission wavelength range.

In the embodiment, the desired emission wavelength region is a green region. Specifically, the maximum emission wavelength in a dilute toluene solution is 490 nm or more and 530 nm or less.

The properties of the basic skeleton of the organic compound according to the embodiment will be described by comparing with comparative control compounds having similar structures to that of the organic compound of the present invention. Specifically, the comparative control compounds are represented by the Formulae (2) and (3).

[Chem. 4]

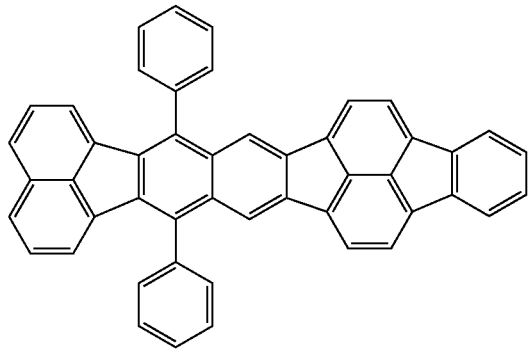

(2)

[Chem. 5]

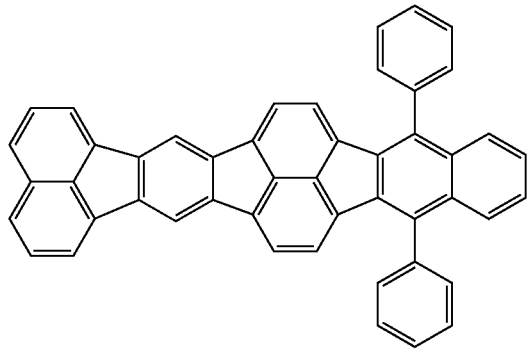 [SMILES: c1ccc(-c2c3c(c(-c4ccccc4)c4ccccc24)-c2ccc4c5cc6c(cc5c5ccc-3c2c54)c2cccc3cccc6c32)cc1]

(3)

One example of the organic compound according to the embodiment is a compound represented by Formula (4), where the basic skeleton is represented by Formula (1); $R_1$ to $R_3$, $R_5$ to $R_7$, $R_9$ to $R_{14}$, $R_{16}$ to $R_{18}$, and $R_{20}$ are hydrogen atoms; and $R_4$, $R_8$, $R_{15}$, and $R_{19}$ are phenyl groups.

[Chem. 6]
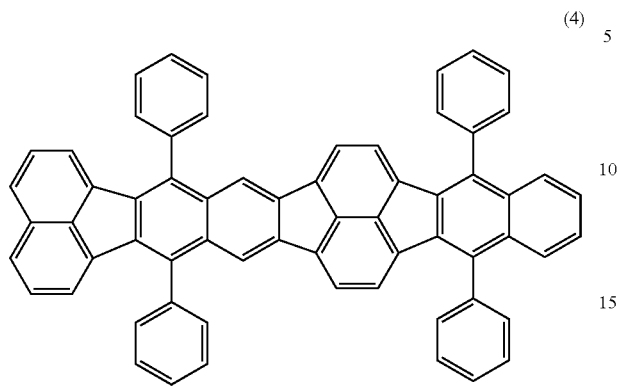
(4)
The present inventors have compared the organic compound represented by Formula (4) with the organic compounds represented by Formulae (2) and (3) for emission wavelength and quantum yield in a dilute toluene solution. The results are shown in Table 1.
TABLE 1
| Compound No. | Structural formula | Maximum emission wavelength (nm) | Quantum yield |
|---|---|---|---|
| 2 | | 520 | <0.1 |
| 3 | | 555 | <0.1 |

TABLE 1-continued

| Compound No. | Structural formula | Maximum emission wavelength (nm) | Quantum yield |
|---|---|---|---|
| 4 | 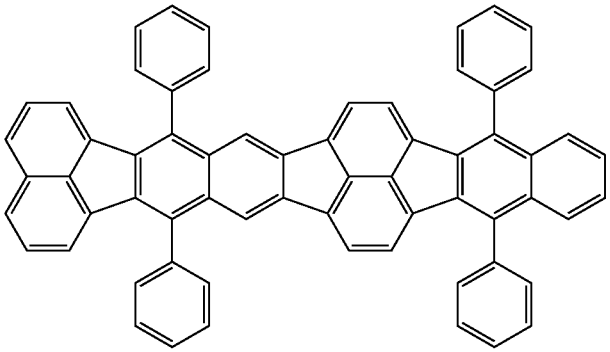 [SMILES: c1ccc(-c2c3c(c(-c4ccccc4)c4ccccc24)-c2ccc4c5cc6c(-c7ccccc7)c7c8cccc9cccc(c7c(-c7ccccc7)c6cc5c5ccc-3c2c54)c98)cc1] | 512 | 0.81 |

The luminescent color of Compound 2 shown in Table 1 is green, but the quantum yield thereof is low, less than 0.1, which is about one-tenth of that of Compound 4. This means that the energy generated when holes and electrons recombine cannot be efficiently converted into light.

The luminescent color of Compound 3 shown in Table 1 is not green, but is yellow, and the quantum yield thereof is low, less than 0.1, which is about one-tenth of that of Compound 4.

Compound 4 shown in Table 1 is an organic compound according to the embodiment and has a high quantum yield compared with those of the above-mentioned materials and has a luminescent color suitable for green of color standards for displays.

Figure 3:
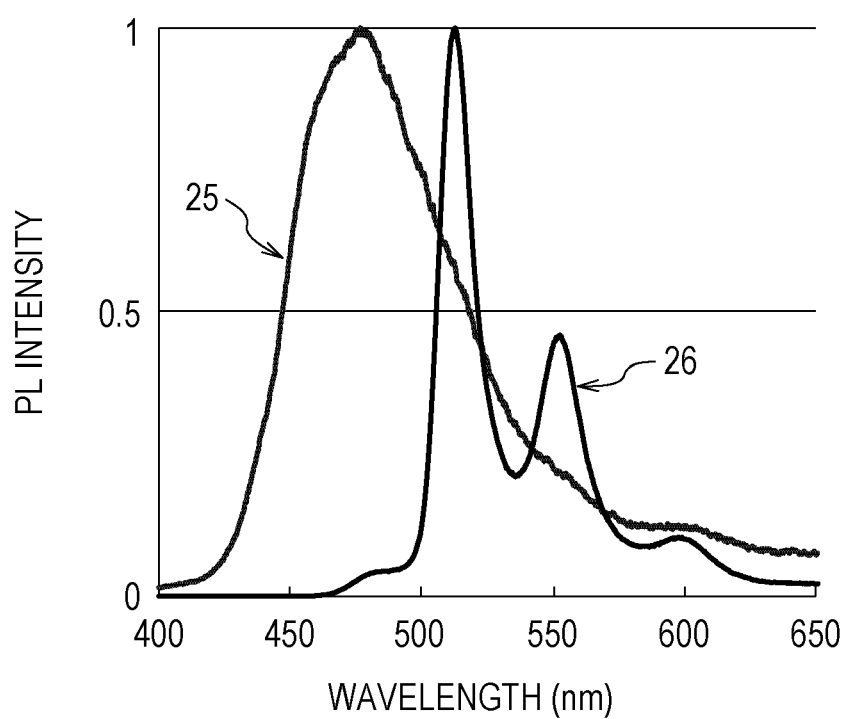
FIG. 3 shows emission spectra of an organic compound according to the embodiment and a comparative organic compound.

FIG. 3 shows spectra of Compound 4 as an organic compound according to the embodiment and Compound 3 as a comparative compound.

In the spectrum of Compound 4 indicated by reference numeral 26, the full width at half maximum of the spectrum at the maximum emission wavelength is 30 nm or less. In contrast, in the spectrum of Compound 3 indicated by reference numeral 25, the full width at half maximum of the spectrum at the maximum emission wavelength is 50 nm or more.

This difference in the width is involved in color purity of the luminescent color. A narrower width means a higher color purity, and a broader width means a lower color purity.

The full width at half maximum in the embodiment is, when the emission intensity of a peak at the maximum emission wavelength of an emission spectrum is normalized as 1, the difference in wavelength of the larger and smaller sides of the peak at an emission intensity of 0.5.

In this point, the luminescent color of the organic compound according to the embodiment has a high purity with respect to a desired color. Thus, the organic compound shows excellent characteristics.

The organic compound according to the embodiment is a material having a high quantum yield of 0.7 or more and is therefore a compound excellent as a green-light-emitting material for organic light-emitting devices. In an organic light-emitting device using a compound having a high quantum yield, the electric power consumption of the device is low.

The basic skeleton of the organic compound according to the embodiment has high flatness and may therefore cause formation of excimers due to intermolecular stacking.

Accordingly, in order to inhibit the generation of excimers, a substituent may be introduced to the compound. A high inhibition effect can be obtained by introducing at least a substituent to one position of $R_4$, $R_7$, $R_8$, $R_{15}$, $R_{16}$, and $R_{19}$, which tend to be orthogonal to the plane formed by the basic skeleton.

That is, the organic compound may have a substituent such as an alkyl group or an aryl group at these positions.

Alternatively, a substituent may be introduced to any position of $R_5$, $R_6$, $R_9$, $R_{10}$, $R_{13}$, $R_{14}$, $R_{17}$, and $R_{18}$, which are effective positions for increasing the intermolecular distance.

The intermolecular stacking can also be inhibited by introducing an alkyl group to the position $R_1$, $R_2$, $R_{10}$, or $R_{13}$ of the organic compound according to the embodiment.

Introduction of an aryl group, a heterocyclic group, or a substituted or unsubstituted amino group to the position $R_{11}$ or $R_{12}$ of the organic compound according to the embodiment can reduce the reactivity of the molecule, resulting in provision of a stable molecule.

The organic compound according to the embodiment has three five-membered ring structures in the basic skeleton and has thereby a low LUMO energy level. This means that the oxidation potential of the compound is low. Therefore, the organic compound according to the embodiment is stable against oxidation.

In the organic compound according to the embodiment, the basic skeleton is constituted of carbon only and does not have any heteroatom such as a nitrogen atom. This also contributes to the low oxidation potential, that is, this is one reason for the stability of the organic compound according to the embodiment against oxidation.

Crystallization of the organic compound molecules according to the embodiment can be inhibited by introducing a substituent to the compound. The inhibition of crystallization leads to inhibition of concentration quenching and to an improvement in sublimability.

Specific examples of the alkyl group as the substituent to be introduced include methyl, ethyl, propyl, butyl, hexyl, and octyl groups. In particular, the substituent can be a sterically large alkyl group such as an isopropyl or tert-butyl group.

Specific examples the aryl group as the substituent to be introduced include phenyl and biphenyl groups. In particular, the substituent can be an aryl group having an alkyl group, such as a methyl, isopropyl, or tert-butyl group.

The same effects can be obtained by introducing a fluorine atom to the organic compound according to the embodiment. The introduction of a fluorine atom also leads to inhibition of concentration quenching and to an improvement in sublimability.

In addition, the introduction of a substituent to the basic skeleton also leads to an improvement in membrane-forming property in a coating method.

Specific examples of the organic compound according to the embodiment are shown below, but the present invention is not limited to them.

[Chem. 7]

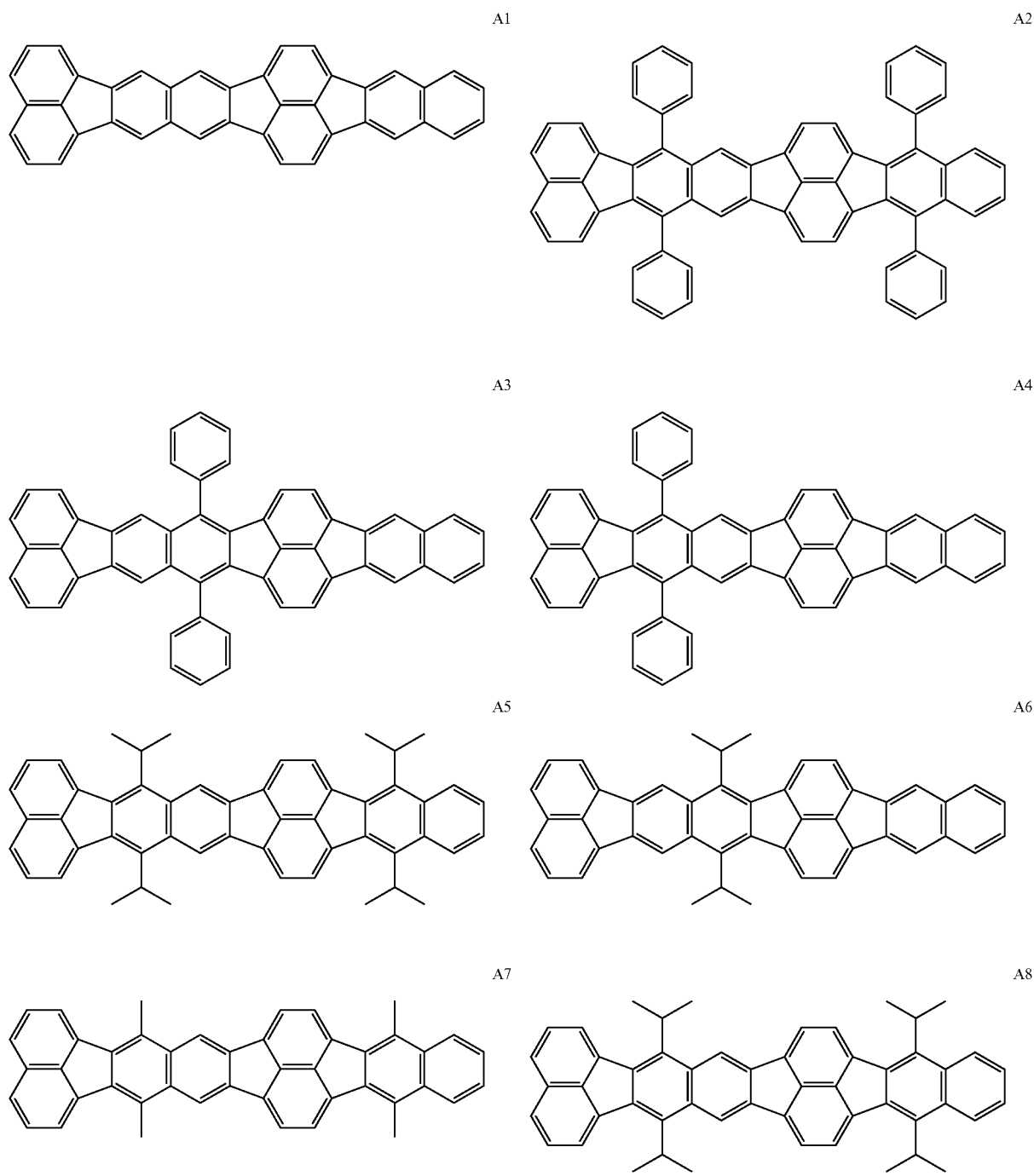

-continued
A9
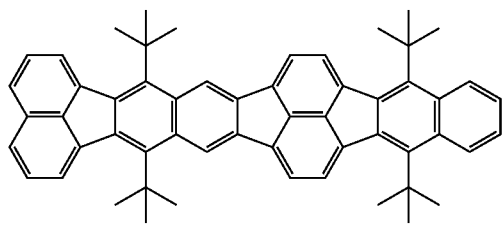
A10
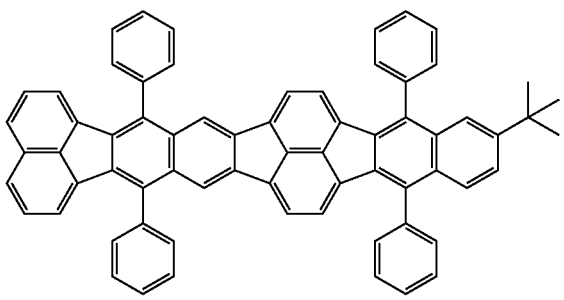
A11
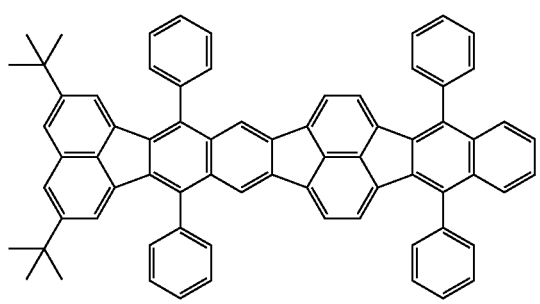
A12
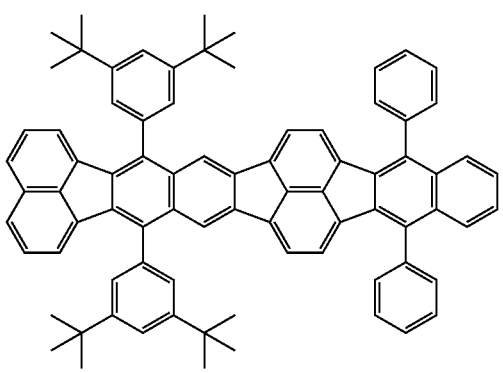
A13
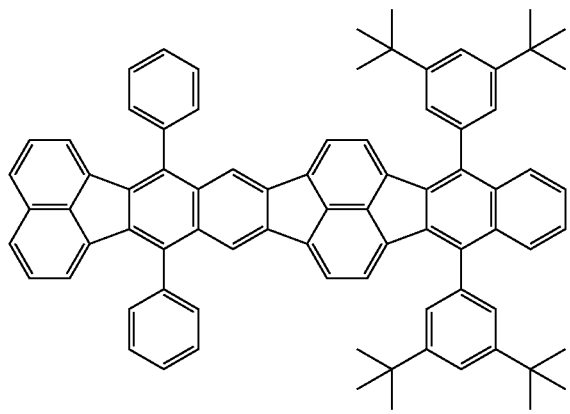
A14
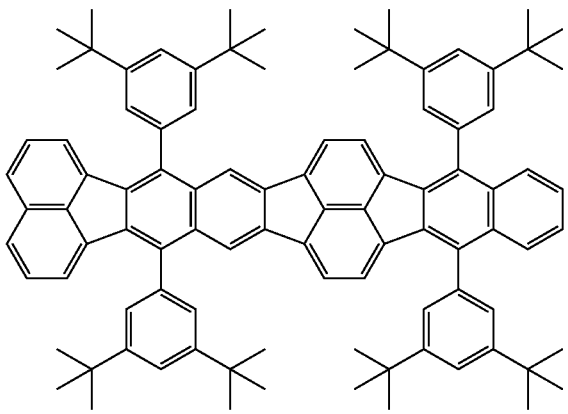
A15
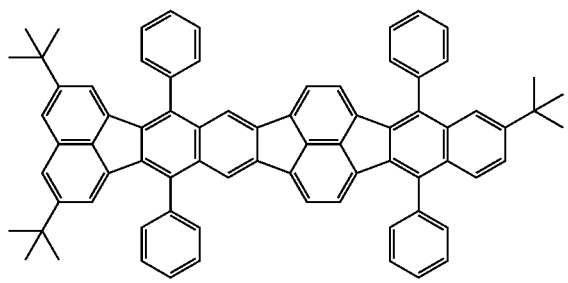
A16
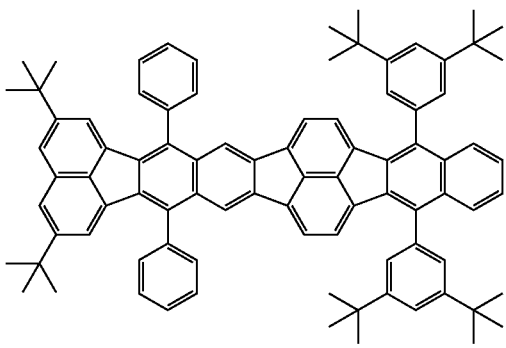

-continued
A17
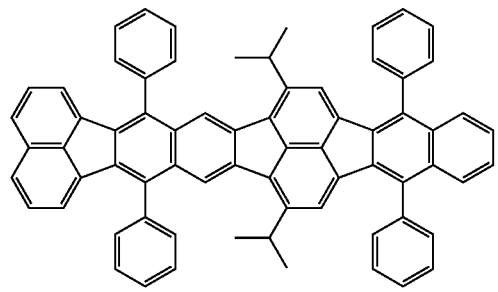
A18
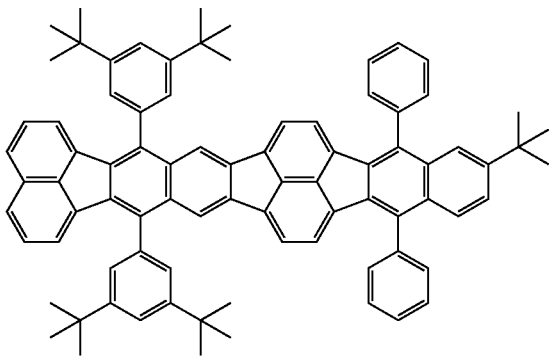
[Chem. 8]
A19
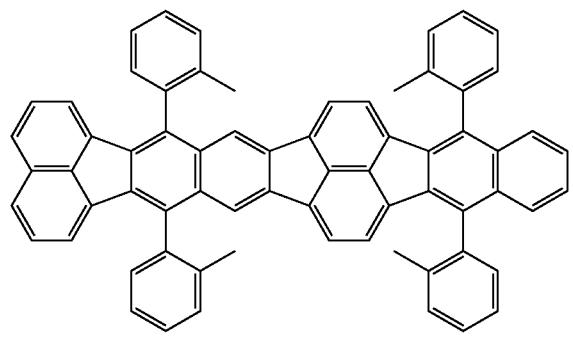
A20
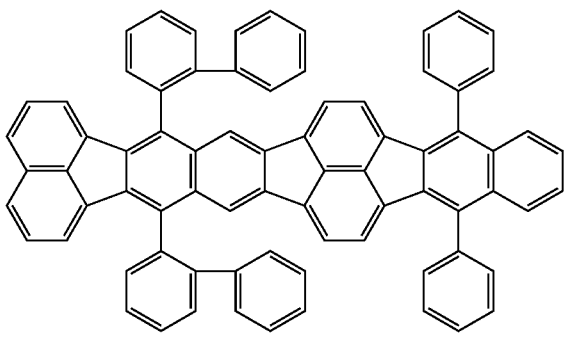
A21
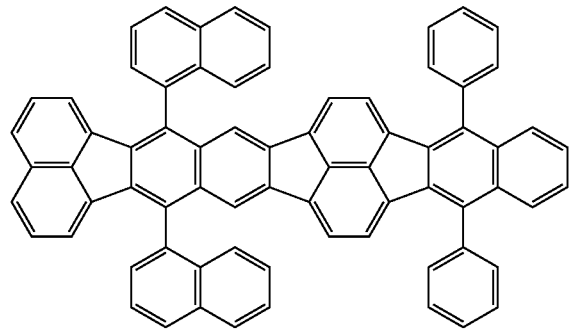
A22
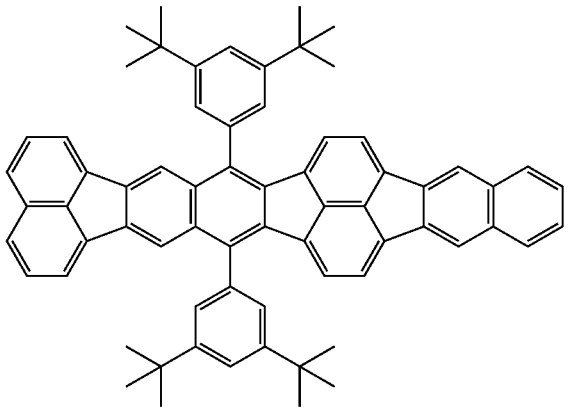
A23
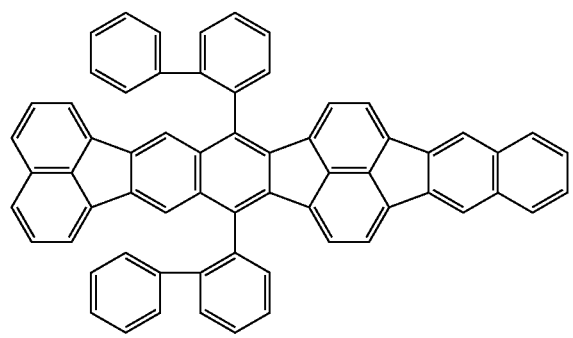
A24
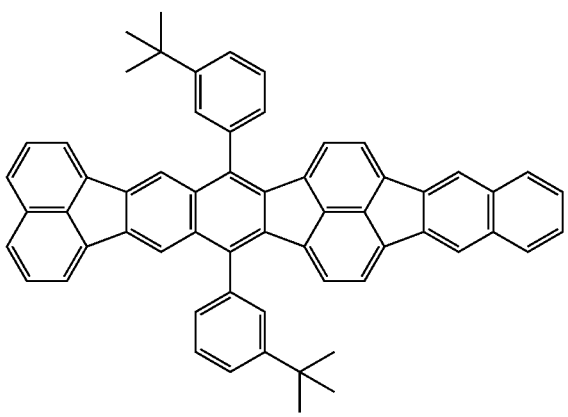

-continued
A25
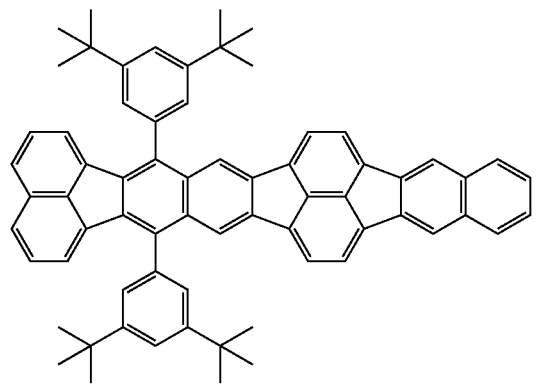
A26
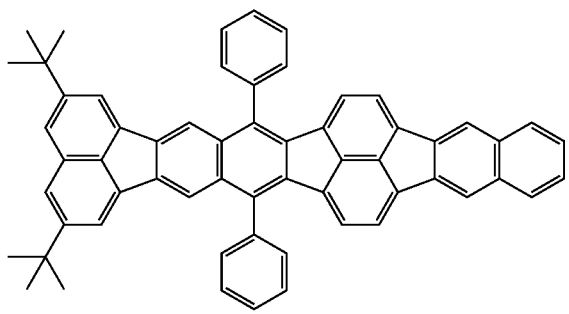
A27
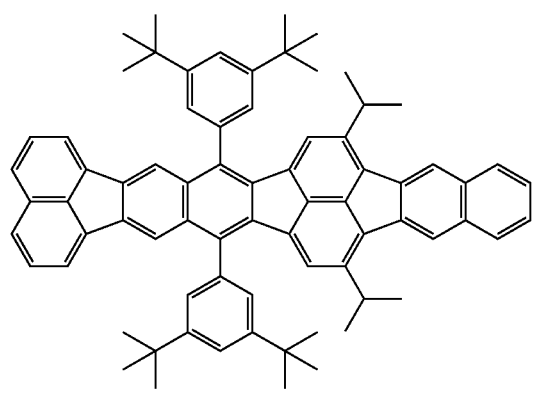
A28
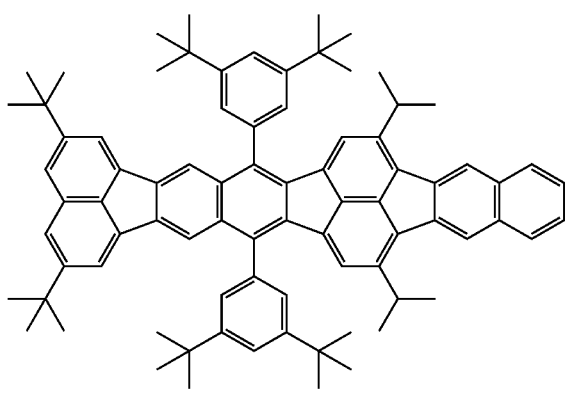
A29
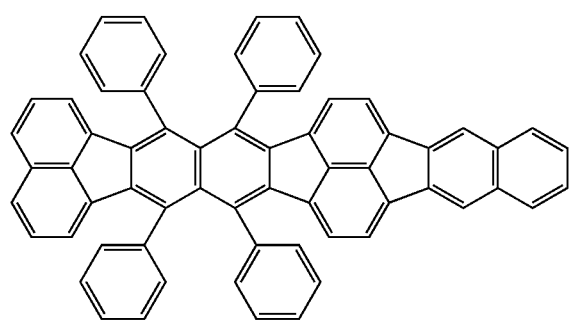
A30
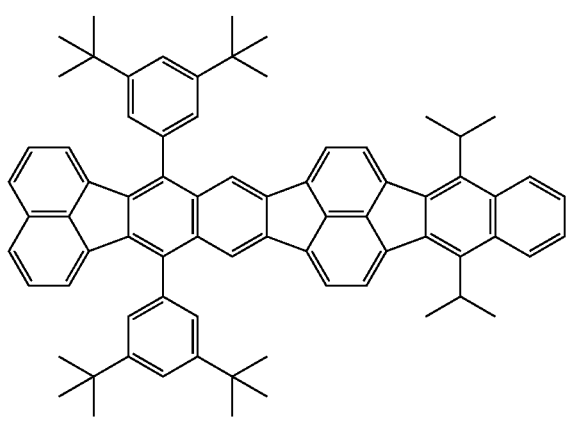

-continued
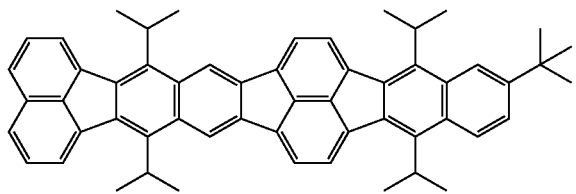
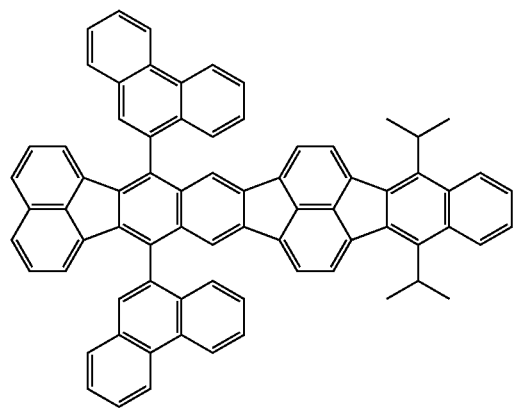
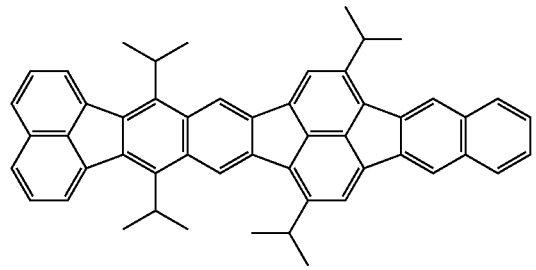
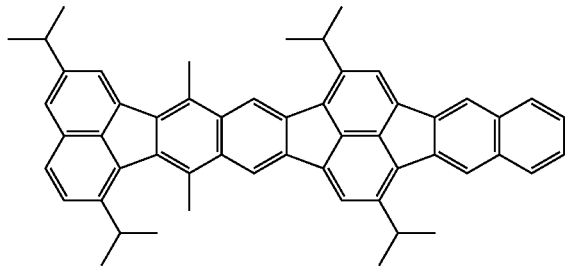
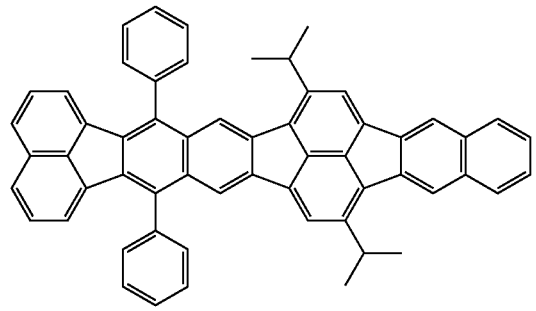
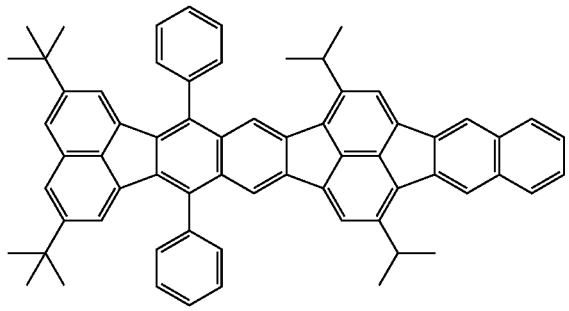
[Chem. 9]
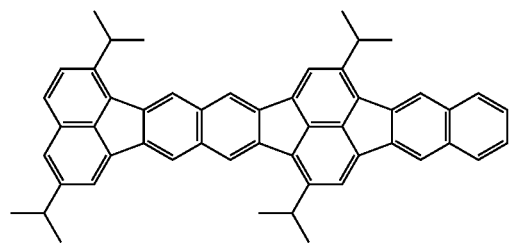
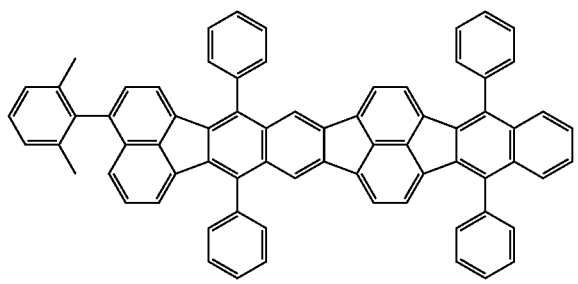

-continued
A39
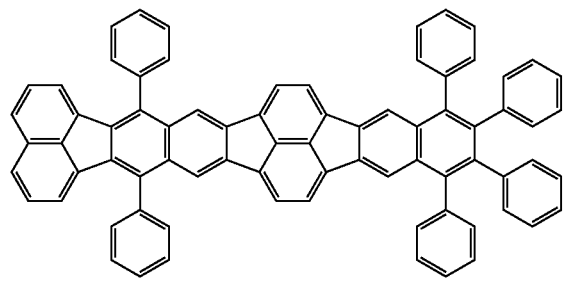
A40
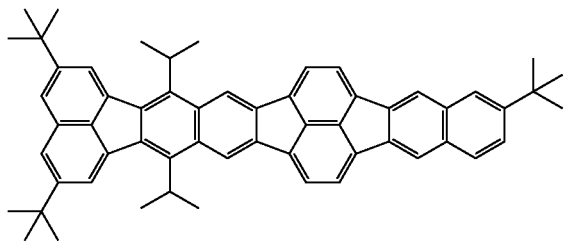
A41
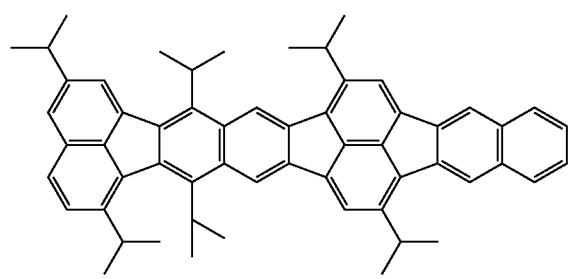
A42
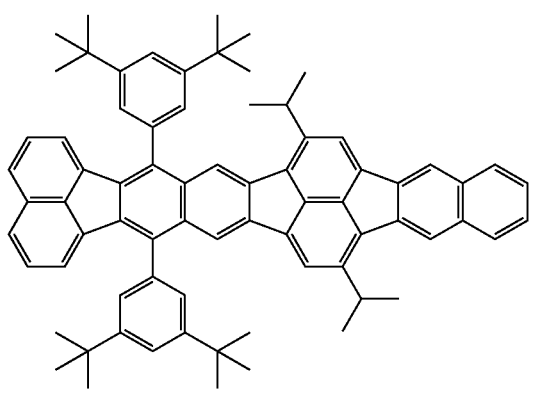
A43
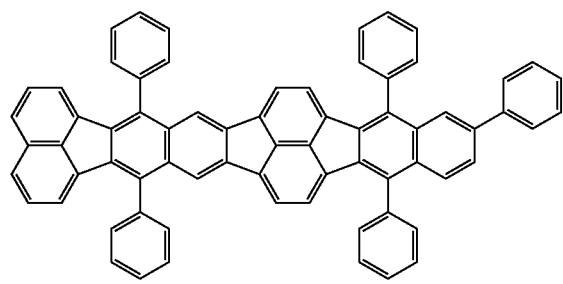
A44
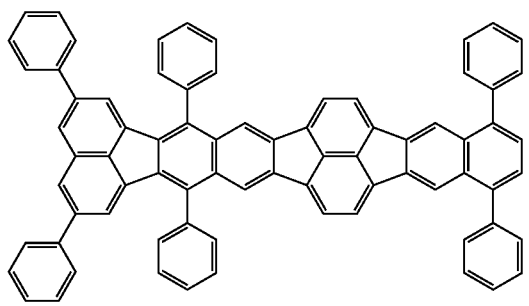
A45
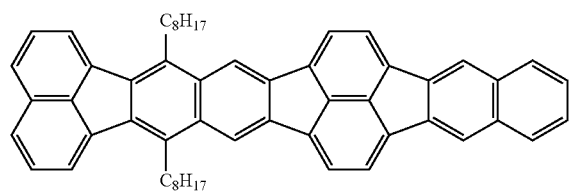
B1
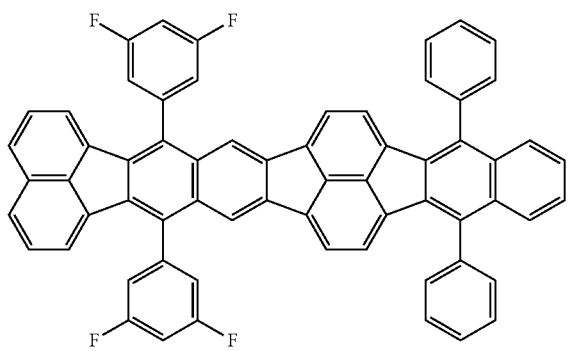

-continued
B2
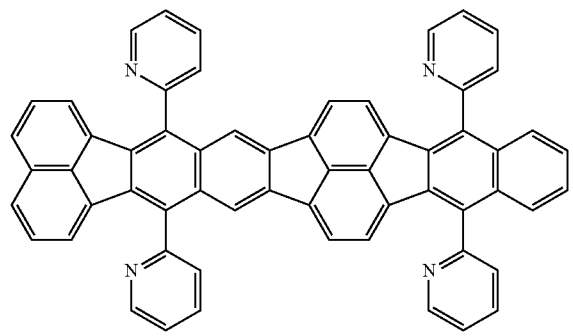
B3
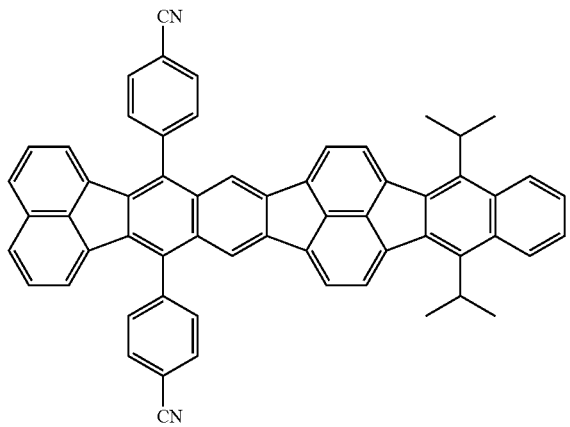
B4
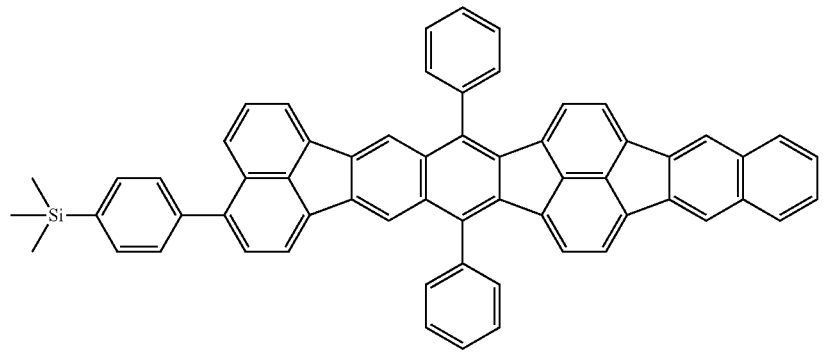
B5
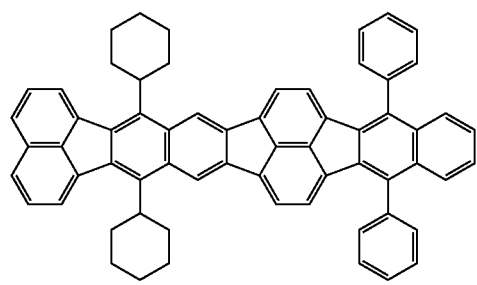
B6
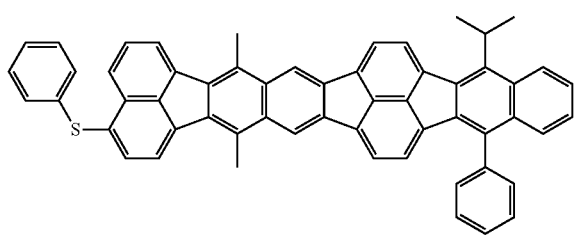
B7
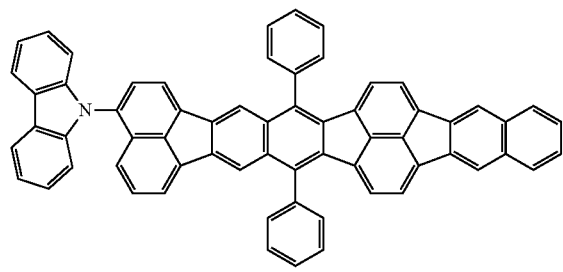
B8
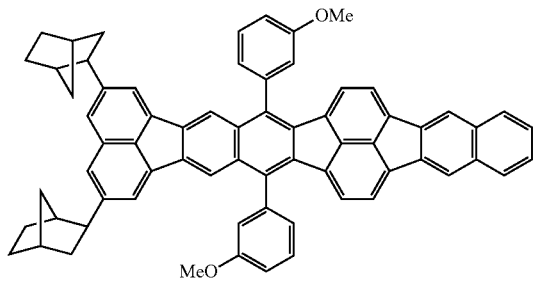

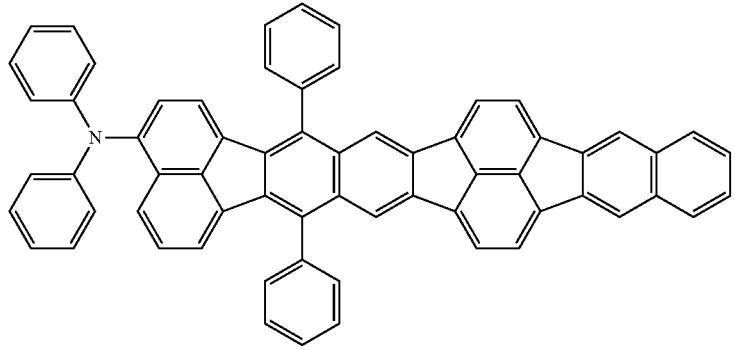

B9

In the example compounds belonging to Group A, the molecule is constituted of hydrocarbons only. Herein, the compounds constituted of hydrocarbons only generally have low LUMO energy levels and are therefore stable against oxidation.

Consequently, among the organic compounds according to the embodiment, compounds constituted of hydrocarbons only, i.e., compounds belonging to Group A, have high molecular stability.

The organic compounds belonging to Group A may be used in a light-emitting layer, a transporting layer, or an injection layer at a high concentration of 100%, but in the use in the light-emitting layer, the concentration can be low.

In the example compounds belonging to Group B, the substituents include heteroatoms. This causes a variation in oxidation potential of the molecule or in intermolecular interaction.

Furthermore, the organic compounds belonging to Group B where the substituents have heteroatoms are useful as electron-transporting, hole-transporting, or hole-trapping light-emitting materials.

In particular, in fluorinated compounds, intermolecular interaction is low, and therefore an improvement in sublimability can be expected. The organic compounds belonging to Group B may be used at a high concentration of 100%.

Synthesis of Organic Compound According to the Embodiment

A method of synthesizing the organic compound according to the embodiment will now be described. The organic compound according to the embodiment can be synthesized in accordance with, for example, the following reaction scheme.

[Chem. 10]

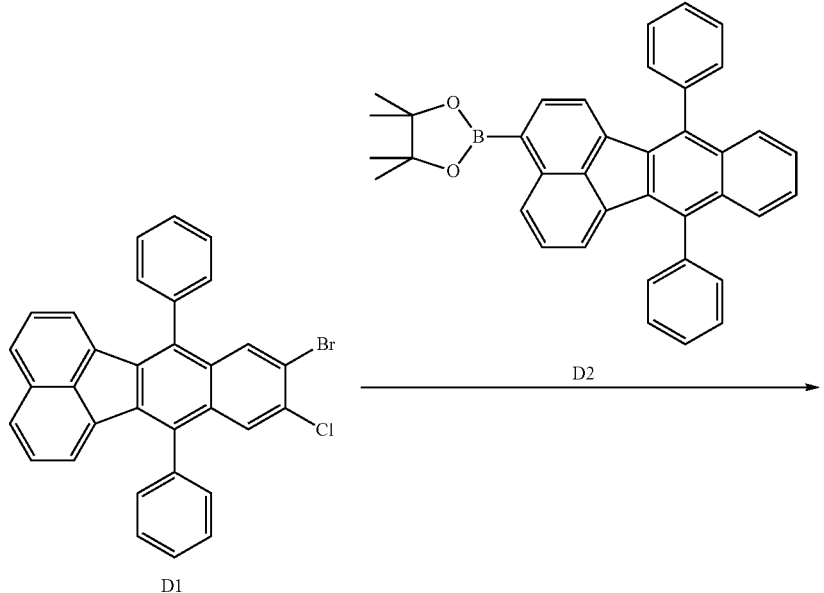

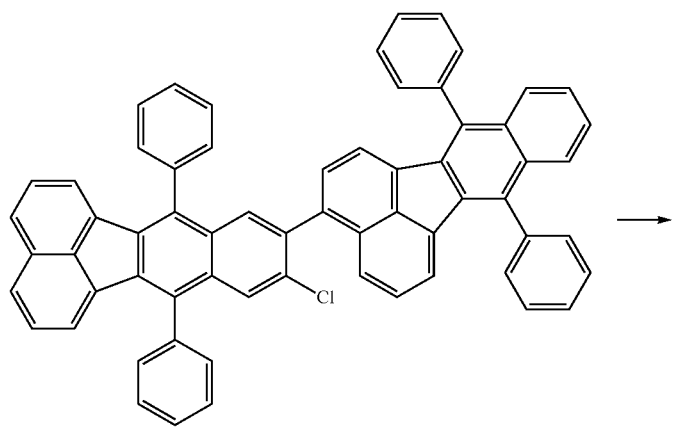
D3
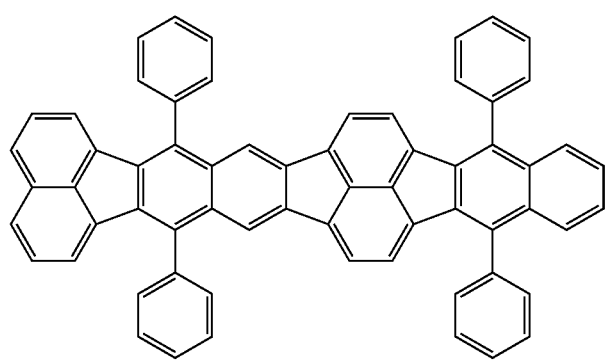
A2
[Chem. 11]
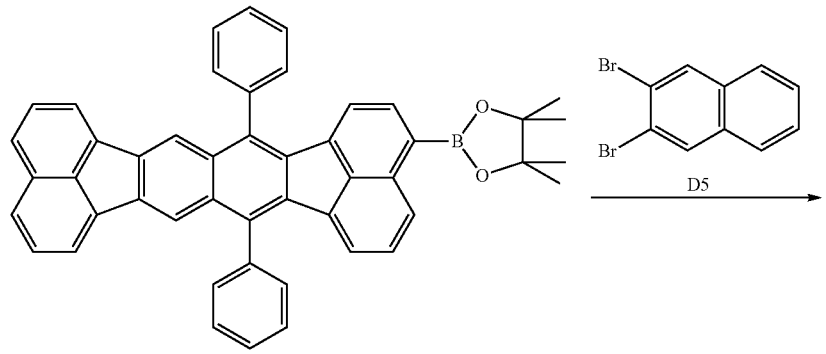
D4
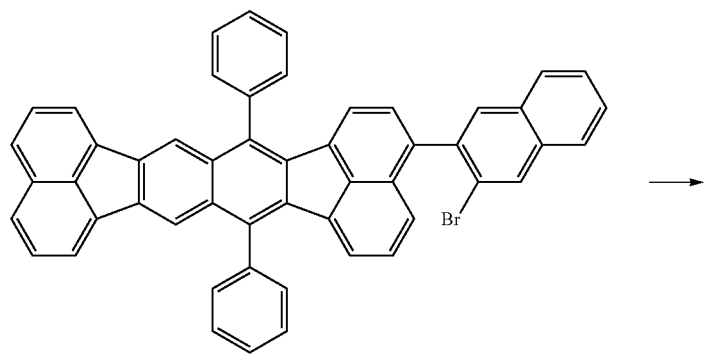
D6

-continued

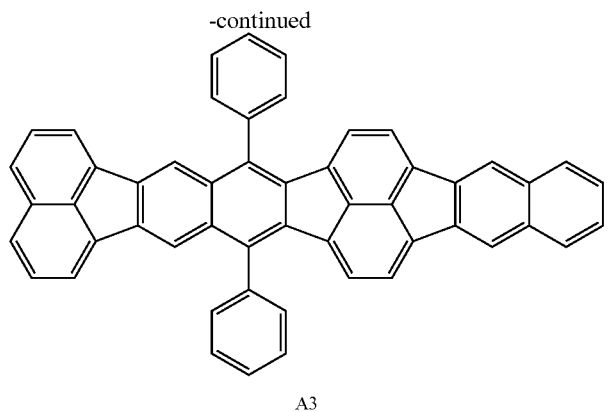

A3

As shown in the synthetic scheme, the organic compound according to the embodiment is synthesized using the following compounds (a) to (d) as raw materials:
(a) benz[k]fluoranthene derivative (D1),
(b) benz[k]fluoranthene derivative (D2),
(c) fluorantheno[8,9-k]fluoranthene derivative (D4), and
(d) naphthalene derivative (D5).

Any of the hydrogen atoms at $R_1$ to $R_{20}$ in Formula (1) is substituted by a predetermined substituent by appropriately introducing the substituent to any of the compounds (a) to (d). Examples of the substituent to be introduced here include alkyl groups, halogen atoms, and phenyl, methoxy, and cyano groups.

Various organic compounds can be synthesized by changing D1 to D4 in the synthetic scheme.

Properties of Organic Light-Emitting Device According to the Embodiment

An organic light-emitting device according to the embodiment will now be described.

The organic light-emitting device according to the embodiment includes an anode and a cathode, as an example of a pair of electrodes, and an organic compound layer disposed between these electrodes.

The organic compound layer of the organic light-emitting device according to the embodiment may be a monolayer or a laminate of a plurality of layers as long as a light-emitting layer is included.

When the organic compound layer is a laminate composed of a plurality of layers, the organic compound layer may include, in addition to a light-emitting layer, for example, a hole-injecting layer, a hole-transporting layer, an electron-blocking layer, a hole/exciton-blocking layer, an electron-transporting layer, and an electron-injecting layer. The light-emitting layer may be a monolayer or a laminate of a plurality of layers.

In the organic light-emitting device according to the embodiment, an organic compound according to the embodiment is contained in at least one layer of the organic compound layers.

In the organic light-emitting device according to the embodiment, the organic compound according to the present invention may be contained in any of the layers and, in particular, can be contained in the light-emitting layer.

When the organic compound according to the embodiment is contained in the light-emitting layer of the organic light-emitting device according to the embodiment, the light-emitting layer may be formed of only the organic compound according to the embodiment or may be formed of the organic compound according to the embodiment and another compound.

In the case of a light-emitting layer made of the organic compound according to the embodiment and another compound, the organic compound according to the embodiment may be used as a host material or a guest material of the light-emitting layer or may be used as an assist material that can be contained in the light-emitting layer.

Throughout the specification, the host material is a compound having a largest weight ratio among the compounds constituting a light-emitting layer, and the guest material is a compound having a smaller weight ratio than that of the host material among the compounds constituting a light-emitting layer and bearing main light emission.

The assist material is a compound having a smaller weight ratio than that of the host material among the compounds constituting a light-emitting layer and assisting the light emission of the guest material. The assist material is also referred to as a second host material.

When the organic compound according to the embodiment is used as a guest material of a light-emitting layer, the concentration of the guest material can be 0.01% by weight or more and 20% by weight or less, in particular, 0.1% by weight or more and 5% by weight or less, based on the total weight of the light-emitting layer.

When the organic compound according to the embodiment is used as a guest material of a light-emitting layer, a material having a higher LUMO level than that of the organic compound according to the embodiment (a material having an LUMO level close to the vacuum level) can be used as the host material.

This is because that since the organic compound according to the embodiment has a low LUMO level, the organic compound according to the embodiment can easily receive electrons supplied by the host material of the light-emitting layer when the host material has a higher LUMO level than that of the organic compound according to the embodiment.

When the organic compound according to the embodiment is used as a host or guest material of a light-emitting layer of an organic light-emitting device, in particular, used as a guest material of the light-emitting layer, the organic light-emitting device has an optical output with high efficiency and high luminance and shows high durability.

The organic light-emitting device according to the embodiment can emit green light, but the luminescent color is not limited to green and can be, for example, white or an intermediate color.

When the organic light-emitting device according to the embodiment emits white light, the light-emitting layers emit light of colors different from each other, i.e., red, green, and blue, and white light is emitted by mixing the respective luminescent colors. The organic compound according to the embodiment can be the material emitting green light.

The organic white-light-emitting device according to the embodiment may be of a configuration having a plurality of light-emitting layers or a configuration having a light-emitting portion including a plurality of light-emitting materials.

FIG. 1 is a schematic cross-sectional view illustrating a device configuration having a lamination type light-emitting layer, which is an example of the organic white-light-emitting device according to the embodiment. This figure shows an organic light-emitting device having three light-emitting layers that emit light of colors different from each other. The structure will be described in detail below.

This organic light-emitting device has a device configuration where an anode 1, a hole-injecting layer 2, a hole-transporting layer 3, a blue-light-emitting layer 4, a green-light-emitting layer 5, a red-light-emitting layer 6, an electron-transporting layer 7, an electron-injecting layer 8, and a cathode 9 are laminated on a substrate such as a glass substrate. The order of the lamination of the blue, green, and red-light-emitting layers may be changed.

The configuration of the light-emitting layers is not limited to lamination, and the layers may be horizontally arranged. In the horizontal arrangement, every light-emitting layer is in contact with the adjacent layers such as a hole-transporting layer and an electron-transporting layer.

The light-emitting layer may have a configuration where a light-emitting layer that emits light of one color includes a domain of a light-emitting layer that emits light of another color.

The light-emitting materials of the blue-light-emitting layer and the red-light-emitting layer are not particularly limited, and examples thereof include compounds having a chrysene skeleton, a fluoranthene skeleton, or an anthracene skeleton; boron complexes; and iridium complexes.

Herein, in addition to the organic compound according to the embodiment, for example, a known low-molecular or high-molecular hole-injecting or transporting compound, host material, light-emitting compound, or electron-injecting or transporting compound can be optionally used.

Examples of these compounds will be shown below.

As the hole-injecting or transporting compound, a material having high hole mobility can be used. Examples of the low or high molecular material having hole-injecting or transporting ability include, but not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

Specific examples of the host material include compounds shown in Table 2.

TABLE 2

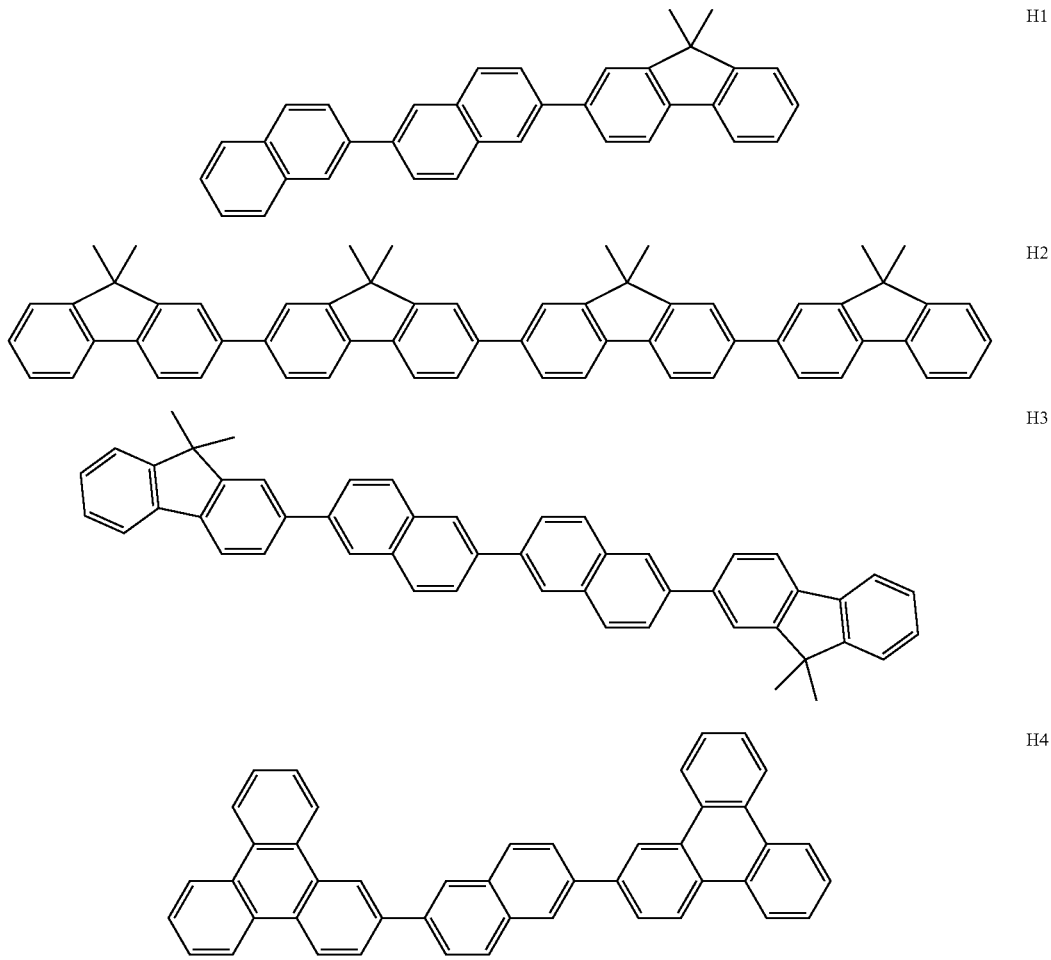

TABLE 2-continued
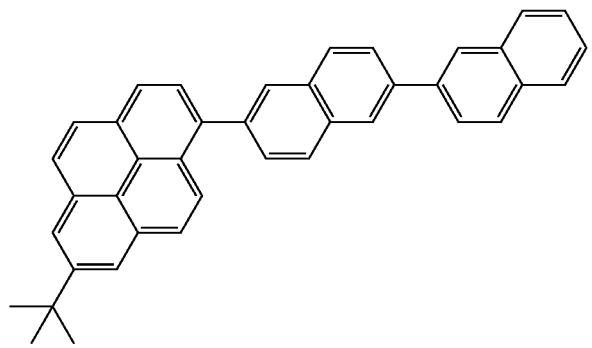 [SMILES: CC(C)(C)c1cc2ccc3ccc(-c4ccc5cc(-c6ccc7ccccc7c6)ccc5c4)c4ccc(c1)c2c34]
H5
H6
H7
H8
H9

TABLE 2-continued
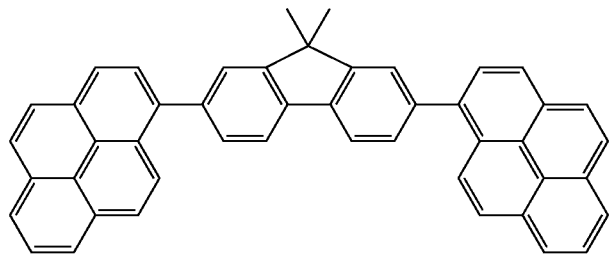 [SMILES: CC1(C)c2cc(-c3ccc4ccc5cccc6ccc3c4c56)ccc2-c2ccc(-c3ccc4ccc5cccc6ccc3c4c56)cc21]
H10
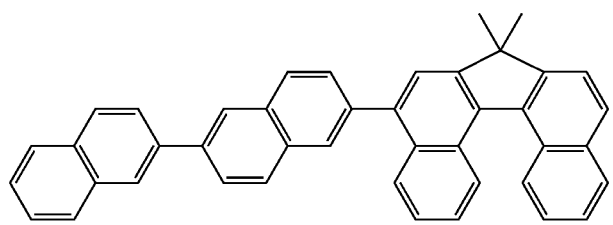 [SMILES: CC1(C)c2ccc3ccccc3c2-c2c1cc(-c1ccc3cc(-c4ccc5ccccc5c4)ccc3c1)c1ccccc21]
H11
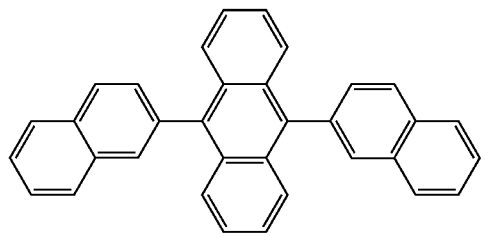 [SMILES: c1ccc2cc(-c3c4ccccc4c(-c4ccc5ccccc5c4)c4ccccc34)ccc2c1]
H12
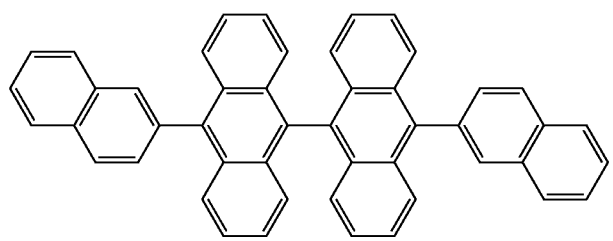 [SMILES: c1ccc2cc(-c3c4ccccc4c(-c4c5ccccc5c(-c5ccc6ccccc6c5)c5ccccc45)c4ccccc34)ccc2c1]
H13
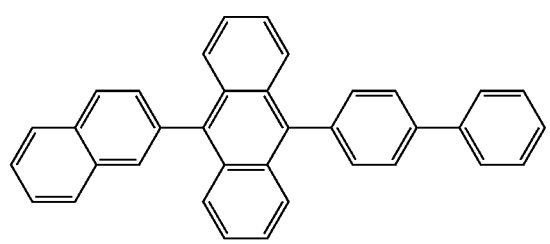 [SMILES: c1ccc(-c2ccc(-c3c4ccccc4c(-c4ccc5ccccc5c4)c4ccccc34)cc2)cc1]
H14
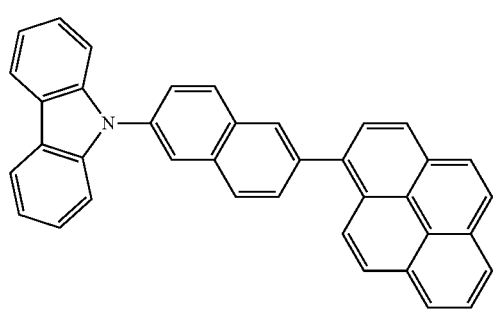 [SMILES: c1cc2ccc3ccc(-c4ccc5cc(-n6c7ccccc7c7ccccc76)ccc5c4)c4ccc(c1)c2c34]
H15

TABLE 2-continued
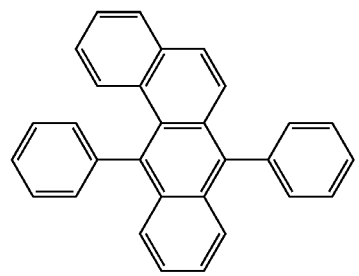 [SMILES: c1ccc(-c2c3ccccc3c(-c3ccccc3)c3c2ccc2ccccc23)cc1]
H16
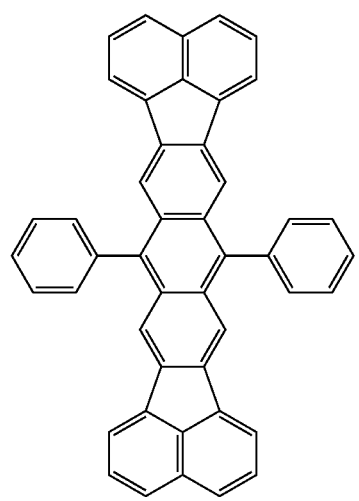 [SMILES: c1ccc(-c2c3cc4c(cc3c(-c3ccccc3)c3cc5c(cc23)-c2cccc3cccc-5c23)-c2cccc3cccc-4c23)cc1]
H17
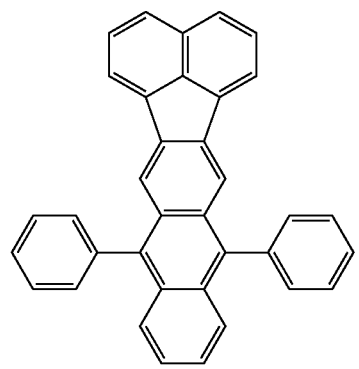 [SMILES: c1ccc(-c2c3ccccc3c(-c3ccccc3)c3cc4c(cc23)-c2cccc3cccc-4c23)cc1]
H18
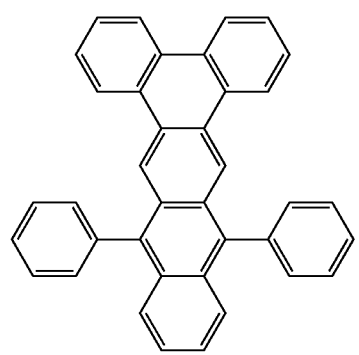 [SMILES: c1ccc(-c2c3ccccc3c(-c3ccccc3)c3cc4c5ccccc5c5ccccc5c4cc23)cc1]
H19

TABLE 2-continued
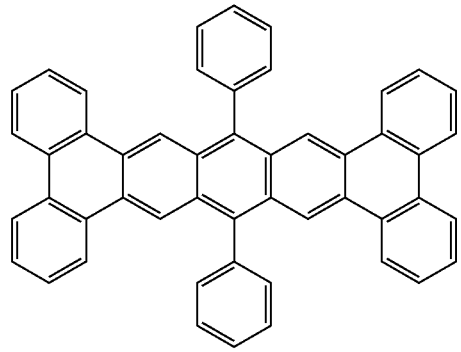 [SMILES: c1ccc(-c2c3cc4c5ccccc5c5ccccc5c4cc3c(-c3ccccc3)c3cc4c5ccccc5c5ccccc5c4cc23)cc1]
H20
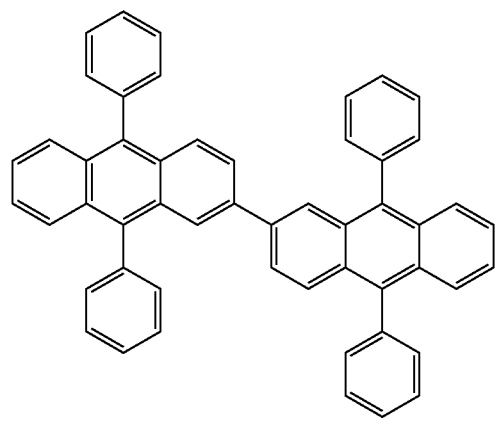 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
H21
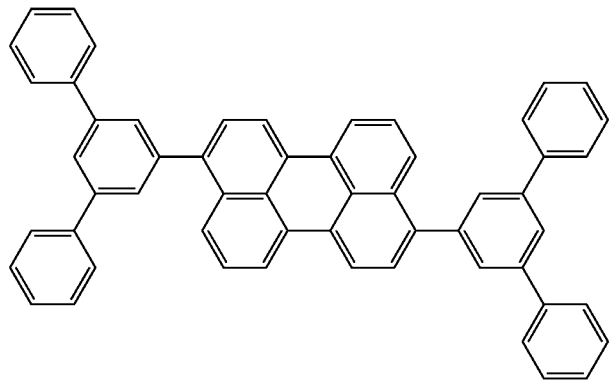 [SMILES: c1ccc(-c2cc(-c3ccccc3)cc(-c3ccc4c5cccc6c(-c7cc(-c8ccccc8)cc(-c8ccccc8)c7)ccc(c7cccc3c74)c65)c2)cc1]
H22
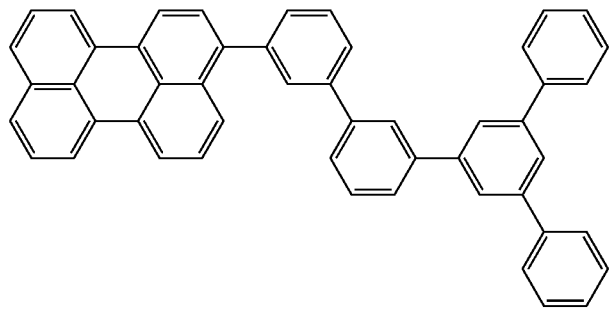 [SMILES: c1ccc(-c2cc(-c3ccccc3)cc(-c3cccc(-c4cccc(-c5ccc6c7cccc8cccc(c9cccc5c96)c87)c4)c3)c2)cc1]
H23

TABLE 2-continued

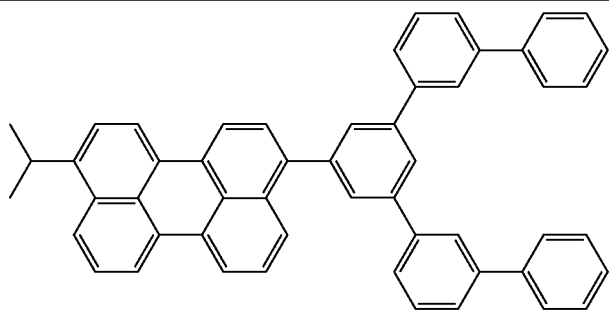

H24

The present invention is not limited thereto. Furthermore, derivatives of the compounds shown in Table 2 also can be used as host materials. In addition, compounds other than the compounds shown in Table 2 can be used as host materials. Examples of such compounds include, but not limited to, fused ring compounds (e.g., fluorene derivatives, naphthalene derivatives, anthracene derivatives, pyrene derivatives, carbazole derivatives, quinoxaline derivatives, and quinoline derivatives), organic aluminum complexes such as tris(8-quinolinolate)aluminum, organic zinc complexes, triphenylamine derivatives, and polymer derivatives such as poly(fluorene) derivatives and poly(phenylene) derivatives.

The electron-injecting or transporting compound are appropriately selected by considering, for example, the balance with the hole mobility of the hole-injecting or transporting compound. Examples of the compound having electron-injecting or transporting ability include, but not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

As the constituent material of the anode, a material having a higher work function is used. Examples thereof include simple metals such as gold, platinum, silver, copper, nickel, palladium, cobalt, selenium, vanadium, and tungsten; alloys of two or more simple metals; and metal oxides such as tin oxide, zinc oxide, indium oxide, indium tin oxide (ITO), and indium zinc oxide. In addition, electrically conductive polymers such as polyaniline, polypyrrole, and polythiophene can be used. These electrode materials may be used alone or in combination. The anode may have a monolayer structure or a multilayer structure.

In contrast, as the constituent material of the cathode, a material having a lower work function is used, and examples thereof include alkali metals such as lithium; alkaline earth metals such as calcium; simple metals such as aluminum, titanium, manganese, silver, lead, and chromium; and alloys of two or more simple metals, such as magnesium-silver, aluminum-lithium, and aluminum-magnesium. In addition, metal oxides such as indium tin oxide (ITO) can be used. These electrode materials may be used alone or in combination. The cathode may have a monolayer structure or a multilayer structure.

In the organic light-emitting device according to the embodiment, a layer containing the organic compound according to the embodiment and layers of other organic compounds are formed by the following methods: In general, thin films are formed by vacuum deposition, ionized vapor deposition, sputtering, plasma coating, or known coating (e.g., spin coating, dipping, a casting method, an LB method, or an ink-jetting method) of compounds dissolved in appropriate solvents. In the case of vacuum deposition, solution coating, or the like, crystallization hardly occurs, and the resulting layer shows excellent stability for a long time. In addition, in coating, a film can be formed in combination with an appropriate binder resin.

Examples of the binder resin include, but not limited to, polyvinyl carbazole resins, polycarbonate resins, polyester resins, ABS resins, acrylic resins, polyimide resins, phenol resins, epoxy resins, silicone resins, and urea resins. These binder resins may be used alone as a homopolymer or a copolymer or in combination of two or more thereof. In addition, known additives such as a plasticizer, an antioxidant, and a UV absorber may be optionally contained in the films.

Use of Organic Light-Emitting Device According to the Embodiment

The organic light-emitting device according to the embodiment can be used as a constituent member of a display apparatus or a lighting system. Other examples of use include exposure light sources of electrophotographic image forming apparatuses, backlights of liquid crystal display apparatuses, and white light sources. The organic light-emitting device may further include a color filter.

The display apparatus includes the organic light-emitting device according to the embodiment in a display section. This display section includes a plurality of pixels, and the pixels each include the organic light-emitting device according to the embodiment and an active device. The anode or the cathode of the organic light-emitting device is connected to the drain electrode or the source electrode of the active device. Here, the display apparatus can be used as a display unit of, for example, a PC.

Examples of the active device include switching devices and amplifier devices, more specifically, transistors and MIM devices. Examples of the transistor include TFT devices.

The display apparatus may be an image information processing apparatus that includes an image input section for inputting image information from, for example, an area CCD, a linear CCD, or a memory card and displays the input image on the display section.

The display apparatus may be a type using a touch panel system for information input.

The lighting system is an apparatus for lighting, for example, a room. The lighting system may emit light of white, natural white, or any color from blue to red. The lighting system includes the organic light-emitting device according to the embodiment and an AC/DC converter connected to the device. The white color has a color temperature of about 4200 K, and the natural white has a color temperature of about 5000 K. The lighting system may have a color filter.

The AC/DC converter according to the embodiment converts AC voltage to DC voltage. The AC/DC converter supplies a driving voltage to the lighting system.

The organic light-emitting device according to the embodiment can be used in an exposure unit of an image-forming apparatus that includes a photosensitive member, a charging unit for charging the photosensitive member, the exposure unit for exposing the photosensitive member, and a developing device for developing an electrostatic latent image formed on the surface of the photosensitive member.

The exposure unit has an exposure light source for exposing the photosensitive member. The exposure light source has a plurality of light emission points arranged in lines. These light emission points can be each independently controlled in light quantity.

A display apparatus using the organic light-emitting device according to the embodiment will now be described with reference to FIG. 2.

Figure 2:
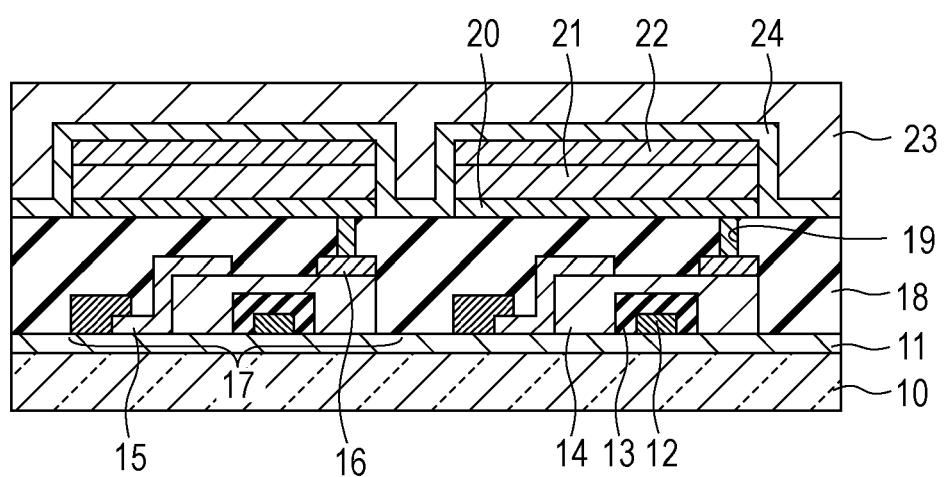
FIG. 2 is a schematic cross-sectional view illustrating a display apparatus having organic light-emitting devices according to the embodiment and TFT devices as an example of switching devices electrically connected to the organic light-emitting devices.

FIG. 2 is a schematic cross-sectional view of a display apparatus having organic light-emitting devices according to the embodiment and TFT devices connected to the organic light-emitting devices.

The display apparatus includes a substrate 10 such as a glass substrate and a moisture-proof film 11 disposed on the substrate 10 for protecting the TFT devices or the organic compound layer. Reference numeral 12 denotes a metal gate electrode, reference numeral 13 denotes a gate insulating film, and reference numeral 14 denotes a semiconductor layer.

The TFT device 17 includes a semiconductor layer 14, a drain electrode 15, and a source electrode 16. An insulating film 18 is disposed on the TFT device 17. The anode 20 of the organic light-emitting device and the source electrode 16 are connected via a contact hole 19.

The display apparatus according to the embodiment is not limited to this configuration as long as either the anode or the cathode is connected to either the source electrode or the drain electrode of the TFT device.

In FIG. 2, the organic compound layer 21 of a multilayer is shown as one layer. The organic compound layer may be a monolayer or multilayer. Furthermore, a first protective layer 23 and a second protective layer 24 are disposed on the cathode 22 to prevent the organic light-emitting device from deteriorating.

When the light emitted by the display apparatus according to the embodiment is white, for example, the lamination type light-emitting layer shown in FIG. 1 is used as the organic compound layer 21 in FIG. 2.

In the organic light-emitting device according to the embodiment, the TFT device as an example of switching device controls the luminance. Organic light-emitting devices disposed in a plurality of planes can display images with the respective luminance.

The switching device of the organic light-emitting device according to the embodiment is not limited to the TFT device and may be a transistor, an MIM device, or an active matrix driver formed on a substrate such as a Si substrate. The transistor formed on a substrate is a transistor directly formed on a substrate such as a Si substrate. This is selected depending on the resolution. For example, in a resolution of about 1-inch QVGA, the active devices can be disposed on a Si substrate.

Display with a good image quality and stability even in long time display can be obtained by driving the display apparatus using the organic light-emitting devices according to the embodiment.

EXAMPLES

The present invention will be described by examples, but is not limited thereto.

Example 1

Synthesis of Example Compound A2

[Chem. 12]

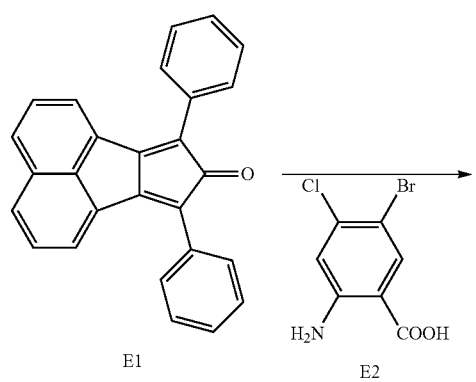

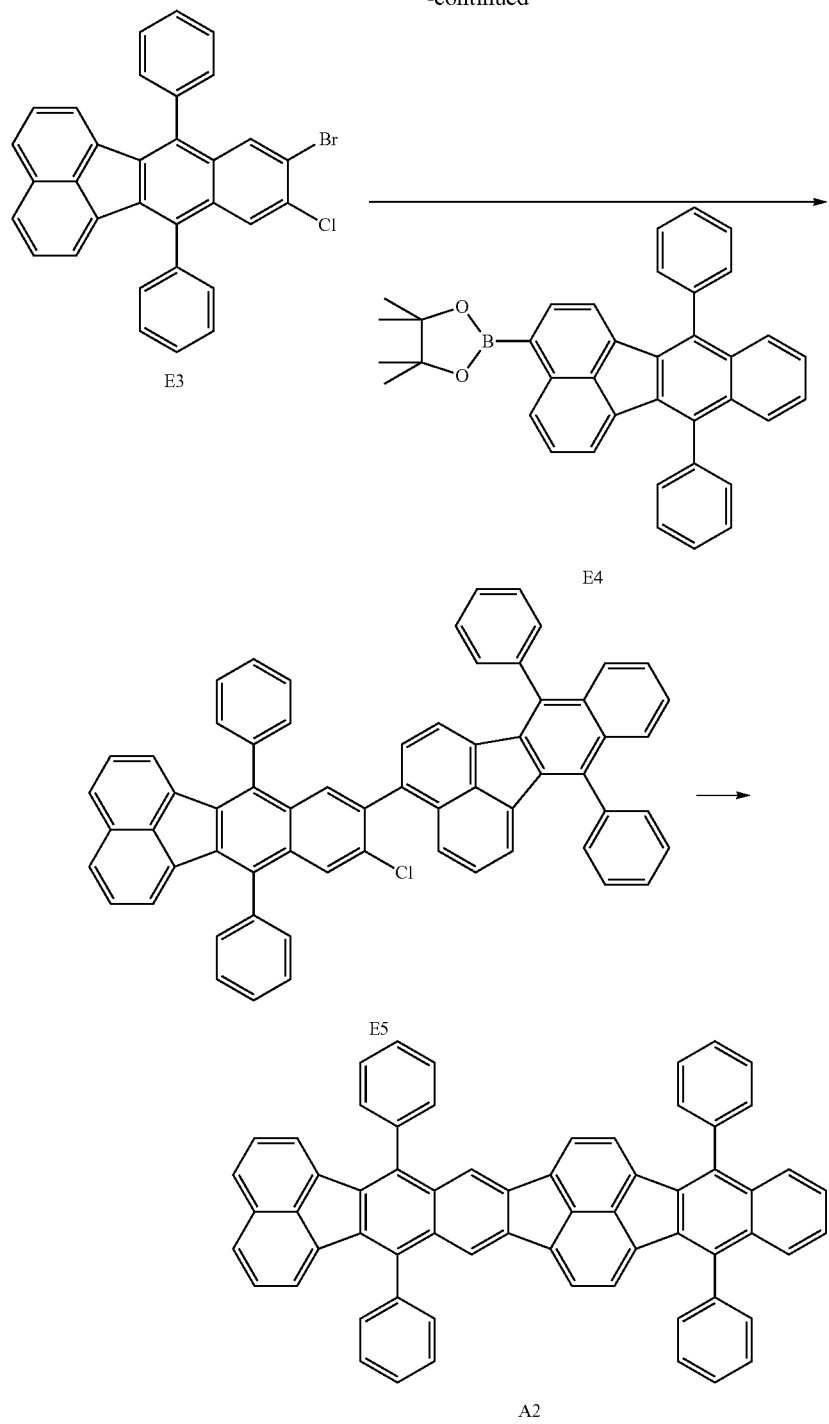

(1) Synthesis of Compound E3

The following reagents and solvents:
Compound E1: 3.56 g (10 mmol),
Compound E2: 3.25 g (13 mmol),
isoamyl nitrite: 1.52 g (13 mmol), and
toluene: 50 mL
were charged in a 100-mL recovery flask.

Then, the reaction solution was heated to 110° C. and stirred at this temperature (110° C.) for 3 hr under a nitrogen gas flow. After completion of the reaction, the organic layer was washed with 50 mL of water twice and then with a saturated saline solution and was dried over magnesium sulfate. The resulting solution was filtered, and the filtrate was concentrated to obtain a dark brown solution. This solution was purified by column chromatography (chloroform:heptane=1:4), followed by recrystallization from chloroform/methanol to obtain 4.3 g (yield: 83%) of Compound E3 as yellow crystals.

(2) Synthesis of Compound E5

The following reagents and solvents:
Compound E4: 2.59 g (5 mmol),
Compound E5: 2.65 g (5 mmol),
Pd(PPh$_3$)$_4$: 0.1 g,
toluene: 50 mL,
ethanol: 20 mL, and
aqueous solution of 2 M sodium carbonate: 50 mL
were charged in a 200-mL recovery flask.

Then, the reaction solution was heated to 80° C. and stirred at this temperature (80° C.) for 8 hr under a nitrogen gas flow. After completion of the reaction, ethanol was added to the reaction solution to precipitate crystals. The crystals were collected by filtration and were washed by dispersing in water, ethanol, and heptane sequentially. Subsequently, the resulting crystals were dissolved in toluene by heating, and the solution was purified by column chromatography (toluene:heptane=1:3), followed by recrystallization from chloroform/methanol to obtain 3.28 g (yield: 78%) of yellow Compound E5.

(3) Synthesis of Example Compound A2

The following reagents and solvents:
Compound E5: 841 mg (1 mmol),
Pd(dba)$_2$: 238 mg,
P(Cy)$_3$ (tricyclohexyl phosphine): 280 mg,
DBU (diazabicycloundecene): 0.15 mL, and
DMF: 5 mL
were charged in a 20-mL recovery flask.

Then, the reaction solution was heated to 145° C. and stirred at this temperature (145° C.) for 6 hr under a nitrogen gas flow. After completion of the reaction, ethanol was added to the reaction solution to precipitate crystals. The crystals were collected by filtration and were washed by dispersing in water, ethanol, and heptane sequentially. Subsequently, the resulting violet crystals were dissolved in toluene by heating, and the solution was filtered in the hot state, followed by recrystallization from toluene/methanol to obtain 0.60 g (yield: 75%) of orange Example Compound A2.

The compound was confirmed to have a purity of 99% or more by HPLC. The emission spectrum of a toluene solution of Example Compound A2 in a concentration of 1×10$^{-5}$ mol/L showed a maximum intensity at 512 nm when the photoluminescence was measured at an excitation wavelength of 350 nm with a fluorospectrophotometer, F-4500, manufactured by Hitachi, Ltd. The mass of Example Compound A2 was analyzed by MALDI-TOF-MS (Autoflex LRF, manufactured by Bruker).

MALDI-TOF-MS

Observed value: m/z=804.11, calculated value: C$_{64}$H$_{36}$=804.28

Example 2

Synthesis of Example Compound A3

[Chem. 13]

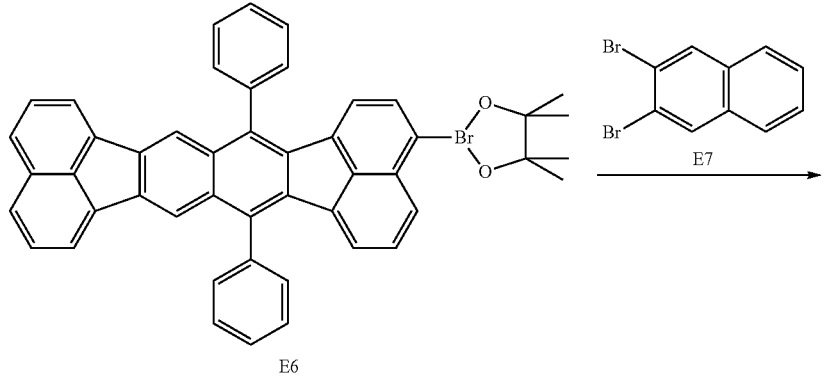

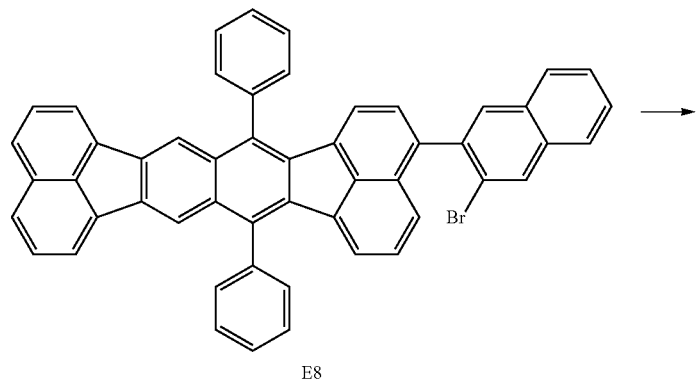

-continued

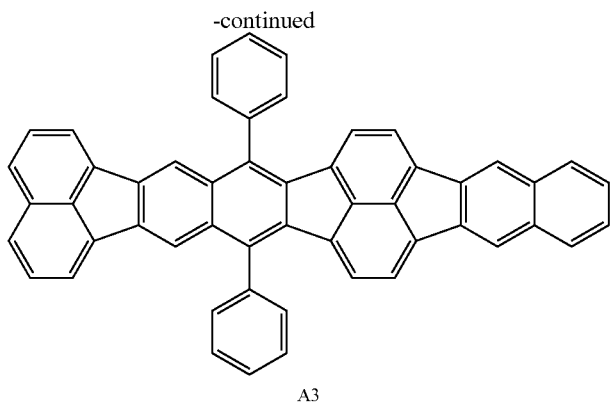

A3

(1) Synthesis of Compound E8

The following reagents and solvents:
Compound E6: 3.27 g (5 mmol),
Compound E7: 1.43 g (5 mmol),
Pd(PPh$_3$)$_4$: 0.1 g,
toluene: 50 mL,
ethanol: 20 mL, and
aqueous solution of 2 M sodium carbonate: 50 mL
were charged in a 200-mL recovery flask.

Then, the reaction solution was heated to 60° C. and stirred at this temperature (60° C.) for 5 hr under a nitrogen gas flow. After completion of the reaction, ethanol was added to the reaction solution to precipitate crystals. The crystals were collected by filtration and were washed by dispersing in water, ethanol, and heptane sequentially. Subsequently, the resulting crystals were dissolved in toluene by heating, and the solution was purified by column chromatography (toluene:heptane=1:3), followed by recrystallization from chloroform/methanol to obtain 2.1 g (yield: 58%) of yellow Compound E8.

(2) Synthesis of Example Compound A3

The following reagents and solvents:
Compound E5: 734 mg (1 mmol),
Pd(dba)$_2$: 238 mg,
P(Cy)$_3$ (tricyclohexyl phosphine): 280 mg,
DBU (diazabicycloundecene): 0.15 mL, and
DMF: 5 mL
were charged in a 20-mL recovery flask.

Then, the reaction solution was heated to 145° C. and stirred at this temperature (145° C.) for 6 hr under a nitrogen gas flow. After completion of the reaction, ethanol was added to the reaction solution to precipitate crystals. The crystals were collected by filtration and were washed by dispersing in water, ethanol, and heptane sequentially. Subsequently, the resulting violet crystals were dissolved in toluene by heating, and the solution was filtered in the hot state, followed by recrystallization from toluene/methanol to obtain 0.43 g (yield: 66%) of orange Example Compound A3.

The purity of the resulting compound was 99% or more when evaluated by HPLC.

The emission spectrum of a toluene solution of Example Compound A3 (concentration: 1×10$^{-5}$ mol/L) showed a maximum intensity at 511 nm when measured by the same method as in Example 1.

The mass of Example Compound A3 was analyzed by MALDI-TOF-MS (Autoflex LRF, manufactured by Bruker).
MALDI-TOF-MS
Observed value: m/z=652.46, calculated value: C$_{52}$H$_{28}$=652.22

Example 3

Synthesis of Example Compound A4

Example Compound A4 was prepared by the same method as in Example 2 except that Compound E9 shown below was used instead of Compound E6 in step (1) of Example 2.

[Chem. 14]

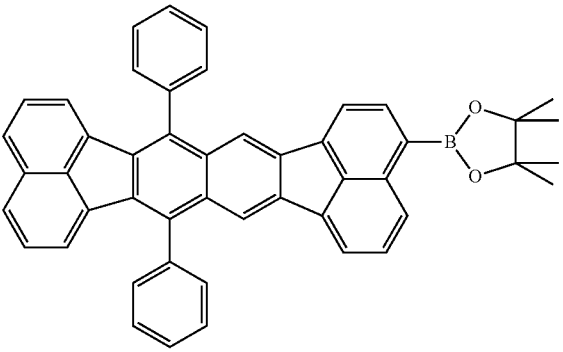

E9

The purity of the resulting compound was 99% or more when evaluated by HPLC.

The emission spectrum of a toluene solution of Example Compound A4 (concentration: 1×10$^{-5}$ mol/L) showed a maximum intensity at 511 nm when measured by the same method as in Example 1.

The mass of Example Compound A4 was analyzed by MALDI-TOF-MS (Autoflex LRF, manufactured by Bruker).
MALDI-TOF-MS
Observed value: m/z=652.48, calculated value: C$_{52}$H$_{28}$=652.22

Example 4

Synthesis of Example Compound A5

Example Compound A5 was prepared by the same method as in Example 1 except that Compounds E10 and E11 shown below were respectively used instead of Compound E1 in step (1) and Compound E4 in step (2) of Example 1.

[Chem. 15]

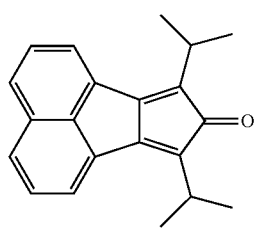
E10

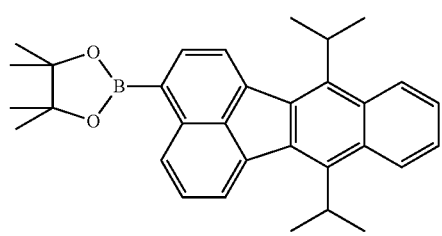
E11

The purity of the resulting compound was 99% or more when evaluated by HPLC.

The emission spectrum of a toluene solution of Example Compound A5 (concentration: $1\times10^{-5}$ mol/L) showed a maximum intensity at 513 nm when measured by the same method as in Example 1.

The mass of Example Compound A5 was analyzed by MALDI-TOF-MS (Autoflex LRF, manufactured by Bruker).
MALDI-TOF-MS
Observed value: m/z=668.50, calculated value: $C_{53}H_{44}$=668.34

Example 5

Synthesis of Example Compound A12

Example Compound A12 was prepared by the same method as in Example 1 except that Compound E12 shown below was used instead of Compound E1 in step (1) of Example 1.

[Chem. 16]

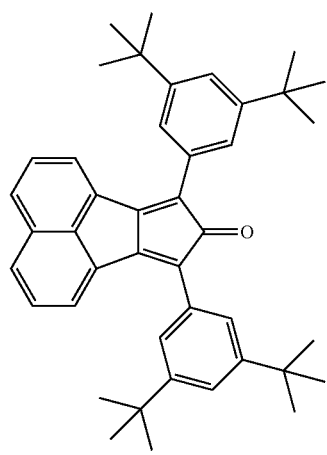
E12

The purity of the resulting compound was 99% or more when evaluated by HPLC.

The emission spectrum of a toluene solution of Example Compound A12 (concentration: $1\times10^{-5}$ mol/L) showed a maximum intensity at 515 nm when measured by the same method as in Example 1.

The mass of Example Compound A12 was analyzed by MALDI-TOF-MS (Autoflex LRF, manufactured by Bruker).
MALDI-TOF-MS
Observed value: m/z=1028.66, calculated value: $C_{80}H_{68}$=1028.53

Example 6

Synthesis of Example Compound A14

Example Compound A14 was prepared by the same method as in Example 1 except that Compounds E13 and E14 shown below were respectively used instead of Compound E1 in step (1) and Compound E4 in step (2) of Example 1.

[Chem. 17]

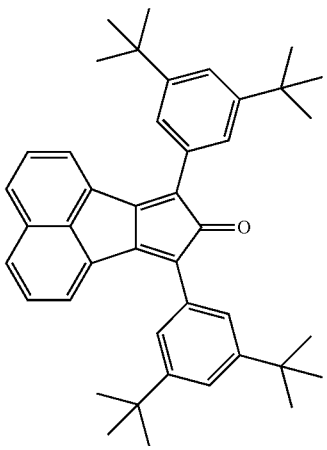
E13

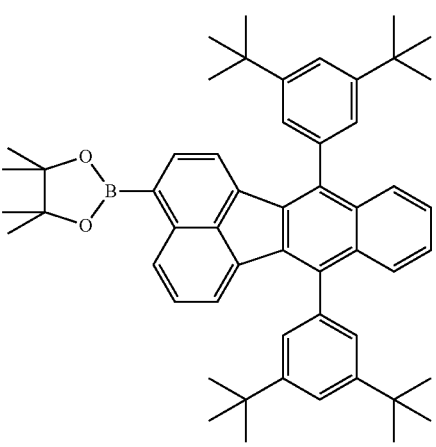
E14

The purity of the resulting compound was 99% or more when evaluated by HPLC.

The emission spectrum of a toluene solution of Example Compound A14 (concentration: $1\times10^{-5}$ mol/L) showed a maximum intensity at 517 nm when measured by the same method as in Example 1.

The mass of Example Compound A14 was analyzed by MALDI-TOF-MS (Autoflex LRF, manufactured by Bruker).

MALDI-TOF-MS

Observed value: m/z=1252.12, calculated value: $C_{96}H_{100}$=1252.78

Example 7

Synthesis of Example Compound A15

Example Compound A15 was prepared by the same method as in Example 1 except that Compounds E15 and E16 shown below were respectively used instead of Compound E1 in step (1) and Compound E4 in step (2) of Example 1.

[Chem. 18]

E15

E16

The purity of the resulting compound was 98% or more when evaluated by HPLC.

The emission spectrum of a toluene solution of Example Compound A15 (concentration: $1\times10^{-5}$ mol/L) showed a maximum intensity at 516 nm when measured by the same method as in Example 1.

The mass of Example Compound A15 was analyzed by MALDI-TOF-MS (Autoflex LRF, manufactured by Bruker).

MALDI-TOF-MS

Observed value: m/z=972.18, calculated value: $C_{76}H_{60}$=972.47

Example 8

Synthesis of Example Compound A16

Example Compound A16 was prepared by the same method as in Example 1 except that Compounds E17 and E18 shown below were respectively used instead of Compound E1 in step (1) and Compound E4 in step (2) of Example 1.

[Chem. 19]

E17

E18

The purity of the resulting compound was 99% or more when evaluated by HPLC.

The emission spectrum of a toluene solution of Example Compound A16 (concentration: $1\times10^{-5}$ mol/L) showed a maximum intensity at 516 nm when measured by the same method as in Example 1.

The mass of Example Compound A16 was analyzed by MALDI-TOF-MS (Autoflex LRF, manufactured by Bruker).

MALDI-TOF-MS

Observed value: m/z=1140.21, calculated value: $C_{88}H_{84}$=1140.66

Example 9

Synthesis of Example Compound A22

Example Compound A22 was prepared by the same method as in Example 2 except that Compound E19 shown below was used instead of Compound E6 in step (1) of Example 2.

[Chem. 20]

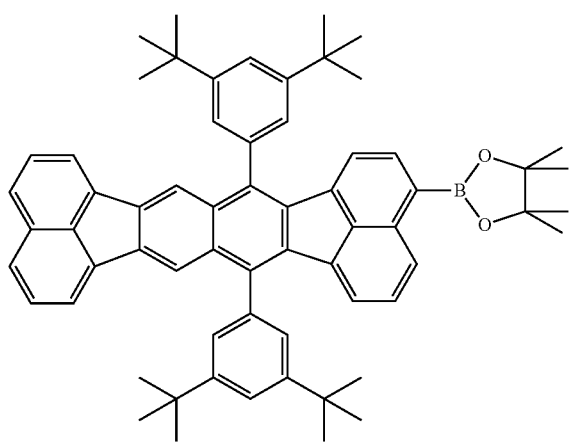

E19

The purity of the resulting compound was 99% or more when evaluated by HPLC.

The emission spectrum of a toluene solution of Example Compound A22 (concentration: 1×10$^{-5}$ mol/L) showed a maximum intensity at 514 nm when measured by the same method as in Example 1.

The mass of Example Compound A22 was analyzed by MALDI-TOF-MS (Autoflex LRF, manufactured by Bruker).

MALDI-TOF-MS

Observed value: m/z=876.44, calculated value: $C_{68}H_{60}$=876.47

Example 10

Synthesis of Example Compound A23

Example Compound A23 was prepared by the same method as in Example 2 except that Compound E20 shown below was used instead of Compound E6 in step (1) of Example 2.

[Chem. 21]

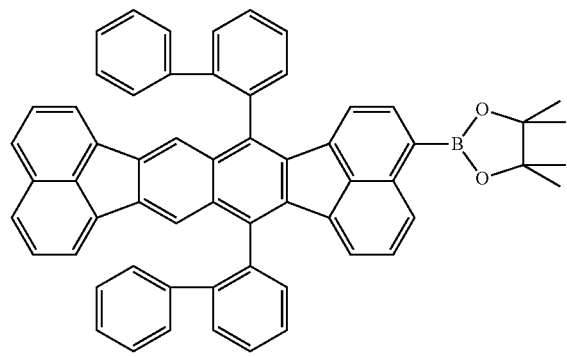

E20

The purity of the resulting compound was 97% or more when evaluated by HPLC.

The emission spectrum of a toluene solution of Example Compound A23 (concentration: 1×10$^{-5}$ mol/L) showed a maximum intensity at 514 nm when measured by the same method as in Example 1.

The mass of Example Compound A23 was analyzed by MALDI-TOF-MS (Autoflex LRF, manufactured by Bruker).

MALDI-TOF-MS

Observed value: m/z=804.82, calculated value: $C_{64}H_{36}$=804.28

Example 11

Synthesis of Example Compound A33

Example Compound A33 was prepared by the same method as in Example 2 except that Compound E21 shown below was used instead of Compound E6 in step (1) of Example 2.

[Chem. 22]

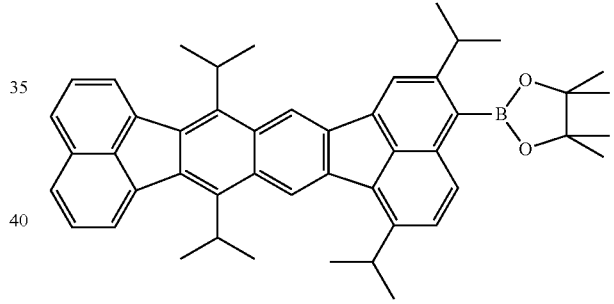

E21

The purity of the resulting compound was 99% or more when evaluated by HPLC.

The emission spectrum of a toluene solution of Example Compound A33 (concentration: 1×10$^{-5}$ mol/L) showed a maximum intensity at 516 nm when measured by the same method as in Example 1.

The mass of Example Compound A33 was analyzed by MALDI-TOF-MS (Autoflex LRF, manufactured by Bruker).

MALDI-TOF-MS

Observed value: m/z=668.56, calculated value: $C_{52}H_{44}$=668.34

Example 12

Synthesis of Example Compound A42

Example Compound A42 was prepared by the same method as in Example 2 except that Compound E22 shown below was used instead of Compound E6 in step (1) of Example 2.

[Chem. 23]

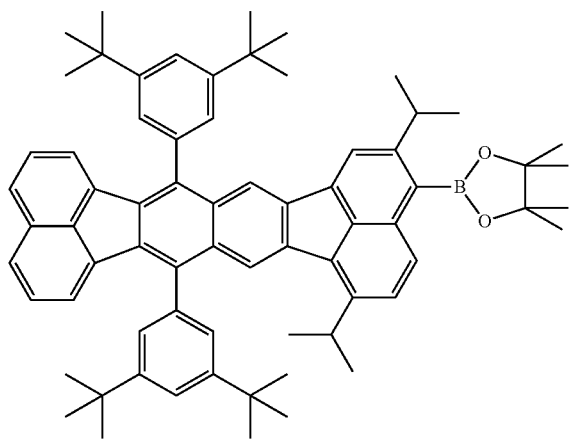

E22

The purity of the resulting compound was 98% or more when evaluated by HPLC.

The emission spectrum of a toluene solution of Example Compound A42 (concentration: 1×10⁻⁵ mol/L) showed a maximum intensity at 516 nm when measured by the same method as in Example 1.

The mass of Example Compound A42 was analyzed by MALDI-TOF-MS (Autoflex LRF, manufactured by Bruker).
MALDI-TOF-MS
Observed value: m/z=960.05, calculated value: $C_{74}H_{72}$=960.56

Example 13

Synthesis of Example Compound A45

Example Compound A45 was prepared by the same method as in Example 2 except that Compound E23 shown below was used instead of Compound E6 in step (1) of Example 2.

[Chem. 24]

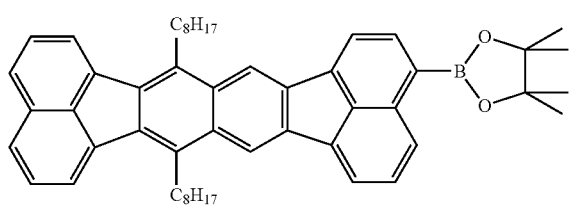

E23

The purity of the resulting compound was 98% or more when evaluated by HPLC.

The emission spectrum of a toluene solution of Example Compound A45 (concentration: 1×10⁻⁵ mol/L) showed a maximum intensity at 517 nm when measured by the same method as in Example 1.

The mass of Example Compound A45 was analyzed by MALDI-TOF-MS (Autoflex LRF, manufactured by Bruker).
MALDI-TOF-MS
Observed value: m/z=724.88, calculated value: $C_{56}H_{52}$=724.41

Example 14

Synthesis of Example Compound B1

Example Compound B1 was prepared by the same method as in Example 1 except that Compound E24 shown below was used instead of Compound E1 in step (1) of Example 1.

[Chem. 25]

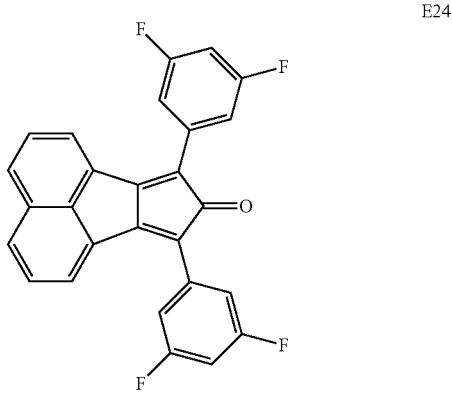

E24

The purity of the resulting compound was 99% or more when evaluated by HPLC.

The emission spectrum of a toluene solution of Example Compound B1 (concentration: 1×10⁻⁵ mol/L) showed a maximum intensity at 510 nm when measured by the same method as in Example 1.

The mass of Example Compound B1 was analyzed by MALDI-TOF-MS (Autoflex LRF, manufactured by Bruker).
MALDI-TOF-MS
Observed value: m/z=807.55, calculated value: $C_{58}H_{36}F_{4}$=808.28

Example 15

Synthesis of Example Compound B9

Example Compound B9 was prepared by the same method as in Example 2 except that Compound E25 shown below was used instead of Compound E6 in step (1) of Example 2.

[Chem. 26]

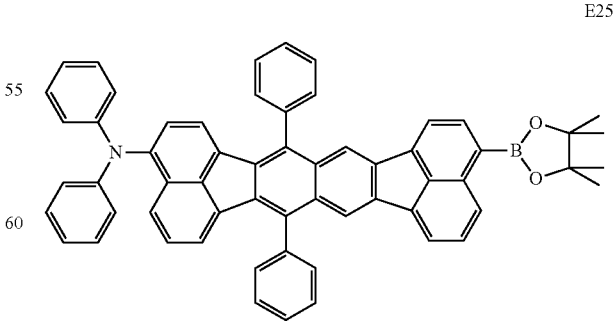

E25

The purity of the resulting compound was 98% or more when evaluated by HPLC.

The emission spectrum of a toluene solution of Example Compound B9 (concentration: 1×10$^{-5}$ mol/L) showed a maximum intensity at 533 nm when measured by the same method as in Example 1.

The mass of Example Compound B9 was analyzed by MALDI-TOF-MS (Autoflex LRF, manufactured by Bruker).

MALDI-TOF-MS

Observed value: m/z=819.86, calculated value: $C_{64}H_{37}N$=819.29

Example 16

In this Example, an organic light-emitting device in which an anode, a hole-transporting layer, an electron-blocking layer, a light-emitting layer, a hole/exciton-blocking layer, an electron-transporting layer, and a cathode were disposed on a substrate in this order was produced. A part of the materials used in this Example are shown below.

[Chem. 27]

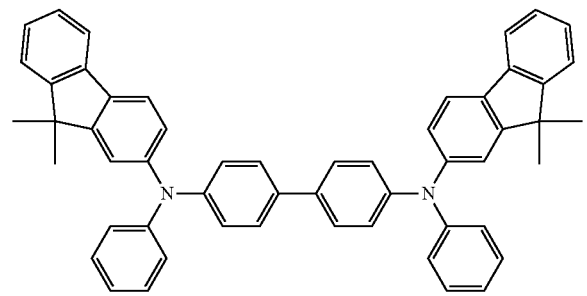

G-1

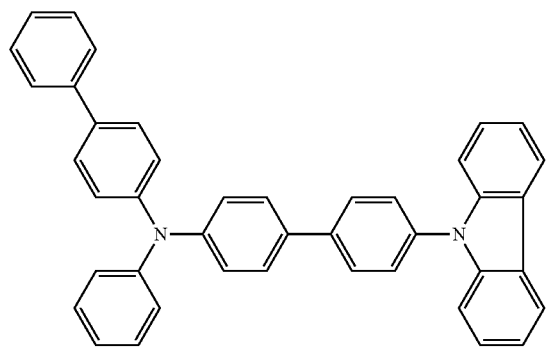

G-2

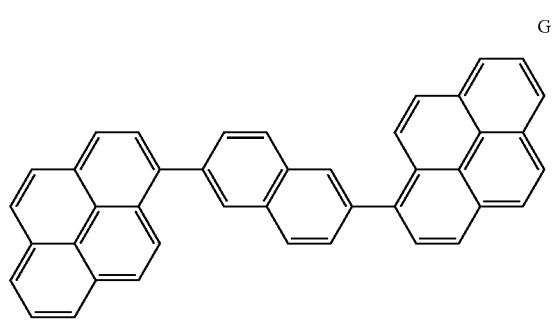

G-5

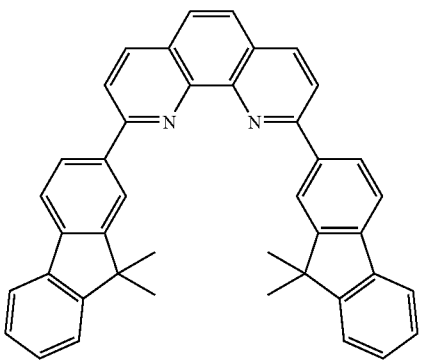

G-6

An ITO film having a thickness of 100 nm was formed on a glass substrate and was formed into an ITO electrode (anode) by patterning. The substrate thus provided with the ITO electrode was used as an ITO substrate in the following steps.

On this ITO substrate, organic compound layers and electrode layers shown in Table 3 were sequentially formed. On this occasion, the area where the electrodes (metal electrode layer, cathode) facing each other was adjusted to be 3 mm$^2$.

TABLE 3

| Material | | Thickness (nm) |
|---|---|---|
| Hole-transporting layer | G-1 | 30 |
| Electron-blocking layer | G-2 | 10 |
| Light-emitting layer | G-3 (host) | 30 |
| | G-4 (assist) | |
| | Example Compound A7 (guest) | |
| | (G-3:G-4:A7 = 60:39.5:0.5 (weight ratio)) | |
| Hole-blocking layer | G-5 | 10 |
| Electron-transporting layer | G-6 | 30 |
| First metal electrode layer | LiF | 1 |
| Second metal electrode layer | Al | 100 |

In this Example, G-3 and G-4 respectively correspond to H10 and H21 shown in Table 2.

The characteristics of the resulting device were measured and evaluated. Specifically, current-voltage characteristics were measured with a microammeter, 4140B, manufactured by Hewlett-Packard Company, and luminance was measured with a luminance meter, BM7, manufactured by Topcon Corp. The measurement results are shown in Table 4.

Examples 17 to 27

Organic light-emitting devices were produced by the same method as in Example 16 except that G-3, G-4, and the guest material were respectively changed to the compounds shown in Table 4. The characteristics of the resulting devices were measured and evaluated as in Example 16. The measurement results are shown in Table 4. In Table 4, G-3 and G-4 are compounds shown in Table 2. In the case where G-3 and G-4 are the same material, the host material and the assist material are the same material.

TABLE 4

| | Guest material | G-3 | G-4 | Luminous efficiency (cd/A) | Voltage (V) |
|---|---|---|---|---|---|
| Example 16 | A12 | H10 | H21 | 39 | 4.0 |
| Example 17 | A2 | H7 | H23 | 35 | 4.0 |
| Example 18 | A3 | H14 | H23 | 38 | 4.1 |
| Example 19 | A12 | H10 | H18 | 36 | 4.0 |
| Example 20 | A13 | H6 | H21 | 39 | 3.9 |
| Example 21 | A14 | H22 | H22 | 30 | 4.0 |
| Example 22 | A15 | H6 | H6 | 38 | 4.2 |
| Example 23 | A16 | H13 | H22 | 39 | 4.1 |
| Example 24 | A22 | H12 | H21 | 37 | 4.0 |
| Example 25 | A22 | H15 | H22 | 35 | 4.1 |
| Example 26 | A33 | H10 | H17 | 38 | 3.9 |
| Example 27 | B1 | H8 | H24 | 38 | 4.1 |

Example 28

In this Example, an organic light-emitting device in which an anode, a hole-injecting layer, a hole-transporting layer, a light-emitting layer, an electron-transporting layer, an electron-injecting layer, and a cathode were disposed on a substrate in this order was produced. The organic light-emitting device produced in this Example has a resonance structure. A part of the materials used in this Example are shown below.

[Chem. 28]

G-11

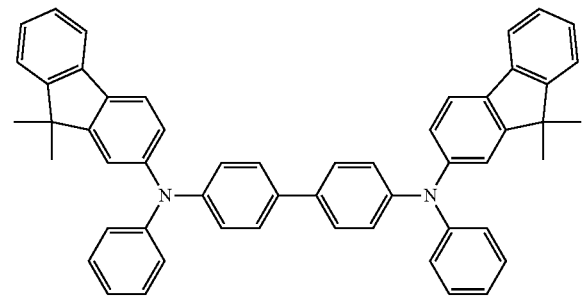

G-12

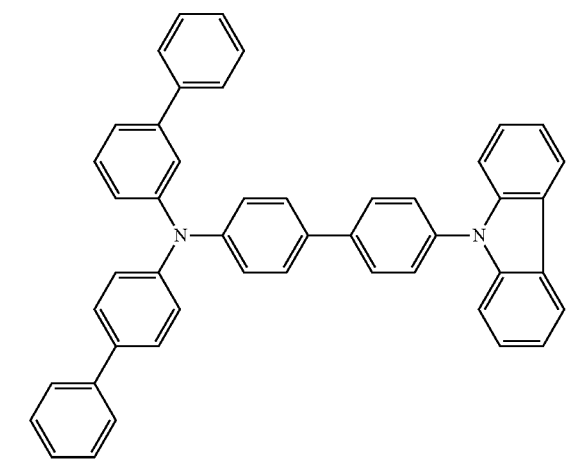

G-13

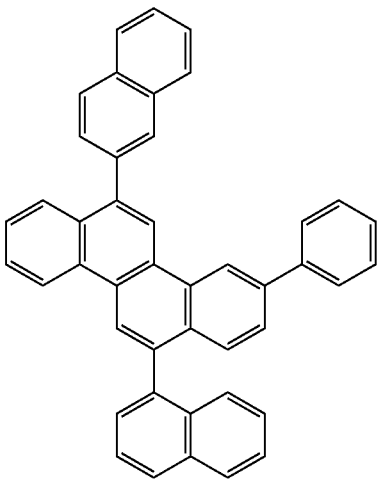

G-14

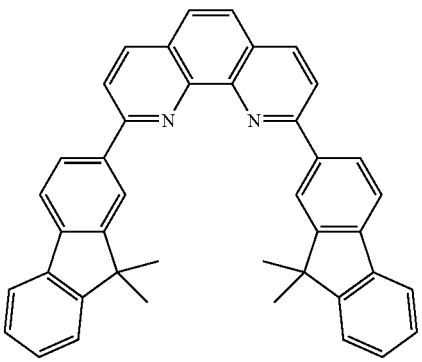

First, a film serving as a reflective anode having a thickness of 100 nm was formed on a glass substrate (support) by sputtering an aluminum alloy (AlNd). Then, a film serving as a transparent anode having a thickness of 80 nm was formed on the reflective anode by sputtering ITO.

Furthermore, a device isolation acrylic film having a thickness of 1.5 μm was formed at the periphery of the anode, and an opening having a radius of 3 mm was formed by patterning.

The substrate provided with the anode was washed by ultrasonic cleaning with acetone and then isopropyl alcohol (IPA) and then washed by boiling in IPA, followed by drying. Furthermore, the surface of this substrate was washed with UV/ozone.

Then, organic compound layers shown in Table 5 were sequentially formed on the ITO substrate by resistance heating vacuum vapor deposition in a vacuum chamber of $1 \times 10^{-5}$ Pa.

TABLE 5

| | Material | Thickness (nm) |
|---|---|---|
| Hole-transporting layer | G-11 | 90 |
| Electron-blocking layer | G-12 | 10 |
| Light-emitting layer | G-13 (host) G-14 (assist) Example Compound A17 (guest) (G-13:G-14:A2 = 60:39.5:0.5 (weight ratio)) | 30 |

TABLE 5-continued

| Material | | Thickness (nm) |
|---|---|---|
| Electron-transporting layer | G-15 | 10 |
| Electron-injecting layer | G-16 | 70 |
| | Li | |
| | (G-16:Li = 80:20 (weight ratio)) | |

In this Example, G-13 and G-14 respectively correspond to H5 and H19 shown in Table 2.

Then, a film serving as a cathode having a thickness of 30 nm was formed on the electron-injecting layer by sputtering ITO. Lastly, sealing was performed in a nitrogen atmosphere. Thus, an organic light-emitting device was produced.

The characteristics of the resulting device were measured and evaluated. Specifically, current-voltage characteristics were measured with a microammeter, 4140B, manufactured by Hewlett-Packard Company, and luminance was measured with a luminance meter, BM7, manufactured by Topcon Corp. The measurement results are shown in Table 6.

Examples 29 to 32

Organic light-emitting devices were produced by the same method as in Example 28 except that G-13, G-14, and the guest material were respectively changed to the compounds shown in Table 7. The characteristics of the resulting devices were measured and evaluated as in Example 28. The measurement results are shown in Table 6.

In Table 6, in the case where G-13 and G-14 are the same material, the host material and the assist material are the same, and G-13 and G-14 are host materials shown in Table 2.

TABLE 6

| | Guest material | G-13 | G-14 | Luminous efficiency (cd/A) | Voltage (V) |
|---|---|---|---|---|---|
| Example 28 | A2 | H5 | H19 | 50 | 4.4 |
| Example 29 | A12 | H10 | H18 | 54 | 4.6 |
| Example 30 | A13 | H12 | H23 | 53 | 4.6 |
| Example 31 | A16 | H21 | H21 | 53 | 4.3 |
| Example 32 | A22 | H6 | H19 | 54 | 4.4 |

Example 33

In this Example, an organic light-emitting device in which an anode, a hole-transporting layer, a first light-emitting layer, a second light-emitting layer, a hole/exciton-blocking layer, an electron-transporting layer, and a cathode were disposed on a substrate in this order was produced. The organic light-emitting device in this Example has a plurality of light-emitting layers. A part of the materials used in this Example are shown below.

[Chem. 29]

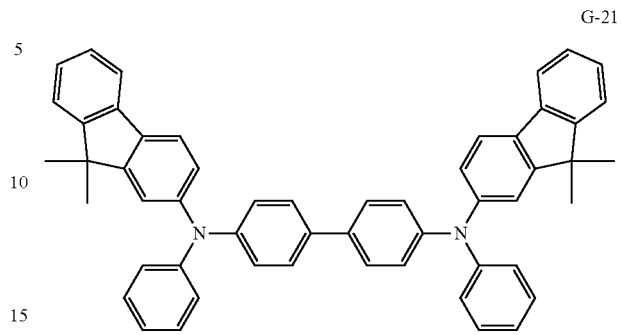

G-21

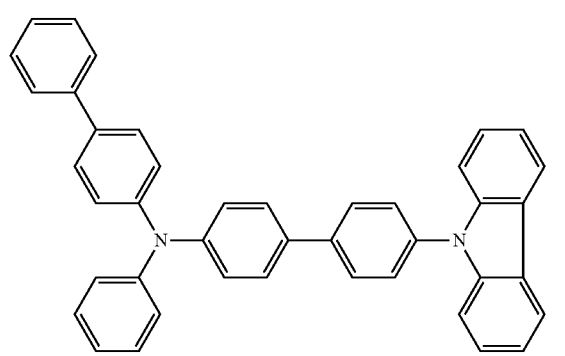

G-22

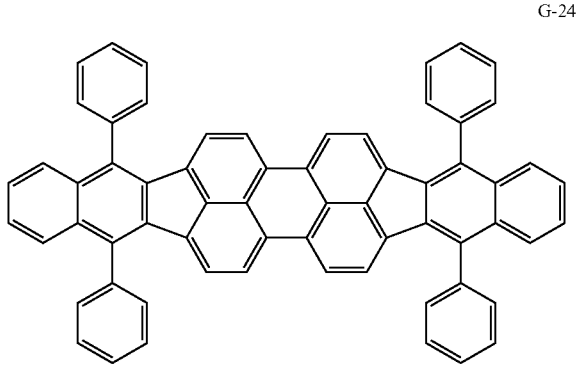

G-24

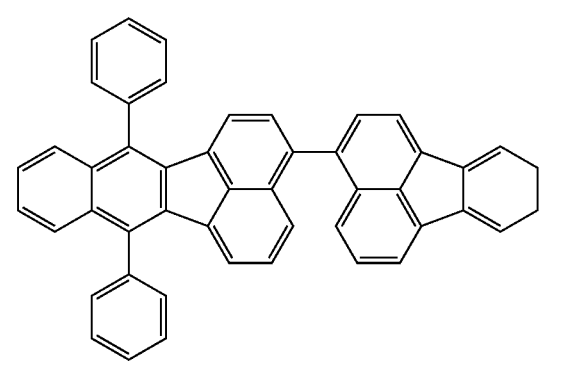

G-26

-continued

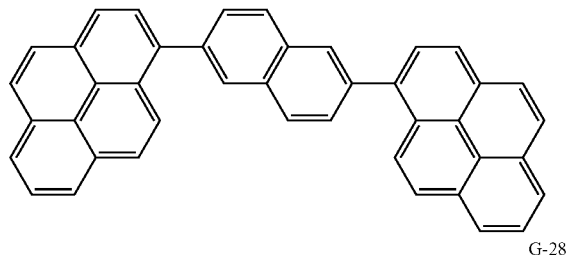

G-27

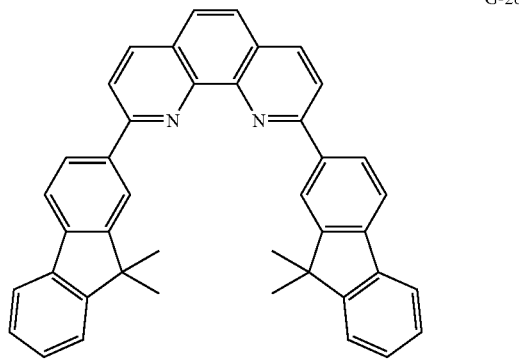

G-28

First, an ITO film having a thickness of 100 nm was formed on a glass substrate and was formed into an ITO electrode (anode) by patterning. The substrate thus provided with the ITO electrode was used as an ITO substrate in the following steps.

Then, organic compound layers and electrode layers shown in Table 7 were sequentially formed on the ITO substrate by resistance heating vacuum vapor deposition in a vacuum chamber of $1\times10^{-5}$ Pa. On this occasion, the area where the electrodes (metal electrode layer, cathode) facing each other was adjusted to be 3 mm$^2$.

TABLE 7

| | Material | Thickness (nm) |
|---|---|---|
| Hole-transporting layer | G-21 | 30 |
| Electron-blocking layer | G-22 | 10 |
| First light-emitting layer | G-23 (first host) G-24 (first guest) Example Compound A18 (second guest) (G-23:G-24:A14 = 95:0.5:4.5 (weight ratio)) | 20 |
| Second light-emitting layer | G-25 (second host) G-26 (third guest) (G-25:G-26 = 96:4 (weight ratio)) | 20 |
| Hole-blocking layer | G-27 | 10 |
| Electron-transporting layer | G-28 | 30 |
| First metal electrode layer | LiF | 1 |
| Second metal electrode layer | Al | 100 |

In this Example, G-23 and G-25 are respectively H10 and H14 shown in Table 2.

The characteristics of the resulting device were measured and evaluated. Specifically, current-voltage characteristics were measured with a microammeter, 4140B, manufactured by Hewlett-Packard Company, and luminance was measured with a luminance meter, BM7, manufactured by Topcon Corp. The measurement results are shown in Table 8.

Examples 34 and 36

Organic light-emitting devices were produced by the same method as in Example 33 except that G-23, G-25, and the guest material were respectively changed to the compounds shown in Table 8. The characteristics of the resulting devices were measured and evaluated as in Example 33. The measurement results are shown in Table 8.

In Table 8, G-23 and G-25 are host materials shown in Table 2.

TABLE 8

| | Guest material | G-23 | G-25 | Luminous efficiency (cd/A) | Voltage (V) |
|---|---|---|---|---|---|
| Example 33 | A14 | H10 | H14 | 14 | 5.2 |
| Example 34 | A12 | H10 | H10 | 15 | 5.2 |
| Example 35 | A15 | H23 | H5 | 13 | 5.3 |
| Example 36 | A18 | H21 | H12 | 13 | 5.1 |

As described by Examples, the organic compounds according to the present invention used in light-emitting devices show chromaticity suitable for green light emission with a narrow full width at half maximum and high efficiency and are therefore excellent green-light-emitting materials. When only the compound of the present invention is used as a light-emitting material, the maximum luminous efficiency is high, i.e., 54 cd/A.

The organic compounds according to the present invention have high quantum yields and emit light suitable for green light emission. Accordingly, organic light-emitting devices including the organic compounds according to the present invention as constituent materials can have excellent light-emitting characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-207325, filed Sep. 22, 2011, which is hereby incorporated by reference herein in its entirety.

REFERENCE SIGNS LIST

4 blue-light-emitting layer

5 green-light-emitting layer

6 red-light-emitting layer

17 TFT device

20 anode

21 organic compound layer

22 cathode

The invention claimed is:

1. An organic compound represented by the following Formula (1):

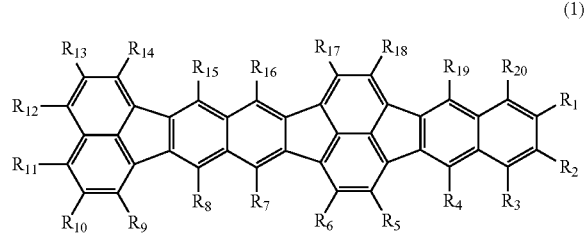

in Formula (1), $R_1$ to $R_{20}$ are each independently selected from hydrogen atoms, halogen atoms, substituted or unsubstituted alkyl groups, substituted or unsubstituted alkoxy groups, substituted or unsubstituted amino groups, substituted or unsubstituted aryl groups, substituted or unsubstituted heterocyclic groups, substituted or unsubstituted aryloxy groups, substituted or unsubstituted thiol groups, silyl groups, and cyano groups.

2. The organic compound according to claim 1, wherein
$R_1$ to $R_{20}$ are each independently selected from hydrogen atoms, substituted or unsubstituted alkyl groups, and substituted or unsubstituted aryl groups.

3. The organic compound according to claim 1, wherein $R_1$ to $R_{20}$ are each independently selected from hydrogen atoms, halogen atoms, substituted or unsubstituted alkyl groups, and substituted or unsubstituted aryl groups, wherein
the alkyl groups have 1 to 4 carbon atoms; and
the aryl groups are a phenyl group or a naphthyl group and optionally have alkyl groups having 1 to 4 carbon atoms.

4. The organic compound according to claim 1, wherein
at least ($R_4$ and $R_{19}$), ($R_7$ and $R_{16}$), or ($R_8$ and $R_{15}$) are alkyl groups or aryl groups.

5. The organic compound according to claim 4, wherein
at least one of $R_1$, $R_2$, $R_{10}$, and $R_{13}$ is an alkyl group.

6. The organic compound according to claim 1, exhibiting green photoluminescence.

7. An organic light-emitting device comprising a pair of electrodes and an organic compound layer disposed between the pair of electrodes, wherein
the organic compound layer contains an organic compound according to claim 1.

8. The organic light-emitting device according to claim 7, wherein
the organic compound layer is a light-emitting layer including a host material and a guest material; and
the guest material is the organic compound.

9. The organic light-emitting device according to claim 8, wherein
the host material has a higher LUMO level than that of the guest material.

10. The organic light-emitting device according to claim 7, emitting green light.

11. The organic light-emitting device according to claim 7, emitting white light, wherein
the organic compound layer includes a plurality of light-emitting layers;
at least one layer of the plurality of light-emitting layers contains the organic compound; and
the plurality of light-emitting layers emit light of colors different from each other.

12. A display apparatus comprising a plurality of pixels, wherein
at least one of the plurality of pixels comprise an organic light-emitting device according to claim 7 and an active device connected to the organic light-emitting device.

13. An image information processing apparatus comprising:
an input section for inputting image information; and
a display section for displaying an image,
wherein the display section is a display apparatus according to claim 12.

14. A lighting system comprising:
an organic light-emitting device according to claim 7; and
an AC/DC converter for supplying a driving voltage to the organic light-emitting device.

15. An image-forming apparatus comprising:
a photosensitive member;
a charging portion for charging a surface of the photosensitive member;
an exposure portion for exposing the photosensitive member; and
a developing device for developing an electrostatic latent image formed on the photosensitive member,
wherein the exposure portion includes an organic light-emitting device according to claim 7.

16. An exposure light source for exposing a photosensitive member, the exposure light source comprising:
a plurality of light emission points arranged in a line, wherein
the light emission points are each independently controlled in light quantity; and
the light emission points each include an organic light-emitting device according to claim 7.

* * * * *